(12) United States Patent
Shelton, IV et al.

(10) Patent No.: US 7,799,039 B2
(45) Date of Patent: Sep. 21, 2010

(54) SURGICAL INSTRUMENT HAVING A HYDRAULICALLY ACTUATED END EFFECTOR

(75) Inventors: Frederick E. Shelton, IV, New Vienna, OH (US); Jerome R. Morgan, Cincinnati, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 957 days.

(21) Appl. No.: 11/270,217

(22) Filed: Nov. 9, 2005

(65) Prior Publication Data
US 2007/0102473 A1 May 10, 2007

(51) Int. Cl.
*A61B 17/10* (2006.01)
(52) U.S. Cl. ............ 606/142; 606/139; 227/175.1
(58) Field of Classification Search ............ 606/142, 606/139; 227/175.1, 180.1
See application file for complete search history.

(56) References Cited

U.S. PATENT DOCUMENTS

| | | | |
|---|---|---|---|
| 1,794,907 A | 3/1931 | Kelly | |
| 2,037,727 A | 4/1936 | Chapelle | |
| 3,551,987 A | 1/1971 | Wilkinson | |
| 3,894,174 A | 7/1975 | Cartun | |
| 3,940,844 A | 3/1976 | Colby et al. | |
| 4,180,285 A | 12/1979 | Reneau | |
| 4,505,273 A | 3/1985 | Braun et al. | |
| 4,520,817 A | 6/1985 | Green | |
| 4,526,174 A | 7/1985 | Froehlich | |
| 4,606,343 A | 8/1986 | Conta et al. | |
| 4,655,222 A | 4/1987 | Florez et al. | |
| 4,709,120 A | 11/1987 | Pearson | |
| 4,809,695 A | 3/1989 | Gwathmey et al. | |
| 4,892,244 A | 1/1990 | Fox et al. | |
| 4,941,623 A | 7/1990 | Pruitt | |
| 4,955,959 A | 9/1990 | Tompkins et al. | |
| 5,005,754 A * | 4/1991 | Van Overloop | 227/178.1 |
| 5,009,661 A | 4/1991 | Michelson | |
| 5,018,657 A * | 5/1991 | Pedlick et al. | 227/178.1 |
| 5,027,834 A | 7/1991 | Pruitt | |
| 5,031,814 A | 7/1991 | Tompkins et al. | |
| 5,040,715 A | 8/1991 | Green et al. | |
| 5,042,707 A | 8/1991 | Taheri | |

(Continued)

FOREIGN PATENT DOCUMENTS

CA 2458946 A1 3/2003

(Continued)

OTHER PUBLICATIONS

Office Action issued on May 2, 2007 in U.S. Appl. No. 11/270,866.

(Continued)

*Primary Examiner*—Julian W Woo
*Assistant Examiner*—Alexander Orkin

(57) ABSTRACT

A hydraulically actuated surgical instrument. The instrument may comprise a handle portion and a shaft. The shaft is mechanically coupled to the handle. The instrument may also include an end effector mechanically coupled to the shaft along its longitudinal axis. The end effector may comprise a surgical implement and a hydraulic device. At least a portion of the surgical implement may be translatable along a transverse axis, wherein the transverse axis is substantially perpendicular to the longitudinal axis of the shaft. Also, the hydraulic device may be positioned to be expandable toward the surgical instrument in a direction substantially parallel to the transverse axis of the shaft.

7 Claims, 19 Drawing Sheets

U.S. PATENT DOCUMENTS

| | | | |
|---|---|---|---|
| 5,071,430 A | 12/1991 | de Salis et al. | |
| 5,080,556 A | 1/1992 | Carreno | |
| 5,084,057 A | 1/1992 | Green et al. | |
| 5,106,008 A | 4/1992 | Tompkins et al. | |
| 5,111,987 A | 5/1992 | Moeinzadeh et al. | |
| 5,116,349 A | 5/1992 | Aranyi | |
| 5,129,570 A | 7/1992 | Schulze et al. | |
| 5,139,513 A | 8/1992 | Segato | |
| 5,156,315 A | 10/1992 | Green et al. | |
| 5,158,567 A | 10/1992 | Green | |
| 5,171,247 A | 12/1992 | Hughett et al. | |
| 5,171,249 A | 12/1992 | Stefanchik et al. | |
| 5,207,697 A | 5/1993 | Carusillo et al. | |
| 5,211,649 A | 5/1993 | Kohler et al. | |
| 5,219,111 A * | 6/1993 | Bilotti et al. | 227/175.1 |
| 5,222,975 A | 6/1993 | Crainich | |
| 5,246,156 A | 9/1993 | Rothfuss et al. | |
| 5,253,793 A | 10/1993 | Green et al. | |
| 5,258,009 A | 11/1993 | Conners | |
| RE34,519 E | 1/1994 | Fox et al. | |
| 5,275,323 A | 1/1994 | Schulze et al. | |
| 5,275,608 A | 1/1994 | Forman et al. | |
| 5,282,806 A | 2/1994 | Haber et al. | |
| 5,282,829 A | 2/1994 | Hermes | |
| 5,304,204 A | 4/1994 | Bregen | |
| 5,307,976 A | 5/1994 | Olson et al. | |
| 5,314,466 A | 5/1994 | Stern et al. | |
| 5,318,221 A | 6/1994 | Green et al. | |
| 5,342,395 A | 8/1994 | Jarrett et al. | |
| 5,342,396 A | 8/1994 | Cook | |
| 5,350,391 A | 9/1994 | Iacovelli | |
| 5,350,400 A | 9/1994 | Esposito et al. | |
| 5,366,479 A | 11/1994 | McGarry et al. | |
| 5,379,933 A | 1/1995 | Green et al. | |
| 5,383,880 A | 1/1995 | Hooven | |
| 5,395,033 A | 3/1995 | Byrne et al. | |
| 5,397,046 A | 3/1995 | Savage et al. | |
| 5,397,324 A | 3/1995 | Carroll et al. | |
| 5,403,312 A | 4/1995 | Yates et al. | |
| 5,405,344 A * | 4/1995 | Williamson et al. | 606/1 |
| 5,413,267 A | 5/1995 | Solyntjes et al. | |
| 5,413,268 A | 5/1995 | Green et al. | |
| 5,415,335 A | 5/1995 | Knodell, Jr. | |
| 5,425,745 A | 6/1995 | Green et al. | |
| 5,431,322 A | 7/1995 | Green et al. | |
| 5,433,721 A | 7/1995 | Hooven et al. | |
| 5,445,304 A | 8/1995 | Plyley et al. | |
| 5,449,365 A | 9/1995 | Green et al. | |
| 5,454,827 A | 10/1995 | Aust et al. | |
| 5,456,401 A | 10/1995 | Green et al. | |
| 5,462,215 A | 10/1995 | Viola et al. | |
| 5,465,895 A | 11/1995 | Knodel et al. | |
| 5,465,896 A | 11/1995 | Allen et al. | |
| 5,470,006 A | 11/1995 | Rodak | |
| 5,472,132 A | 12/1995 | Savage et al. | |
| 5,474,566 A | 12/1995 | Alesi et al. | |
| 5,478,354 A | 12/1995 | Tovey et al. | |
| 5,480,089 A | 1/1996 | Blewett | |
| 5,482,197 A | 1/1996 | Green et al. | |
| 5,484,451 A | 1/1996 | Akopov et al. | |
| 5,485,947 A | 1/1996 | Olson et al. | |
| 5,485,952 A | 1/1996 | Fontayne | |
| 5,487,499 A | 1/1996 | Sorrentino et al. | |
| 5,487,500 A | 1/1996 | Knodel et al. | |
| 5,497,933 A | 3/1996 | DeFonzo et al. | |
| 5,503,320 A | 4/1996 | Webster et al. | |
| 5,509,596 A | 4/1996 | Green et al. | |
| 5,518,163 A | 5/1996 | Hooven | |
| 5,518,164 A | 5/1996 | Hooven | |
| 5,522,817 A | 6/1996 | Sander et al. | |
| 5,529,235 A | 6/1996 | Boiarski et al. | |
| 5,535,934 A | 7/1996 | Boiarski et al. | |
| 5,540,375 A | 7/1996 | Bolanos et al. | |
| 5,542,594 A | 8/1996 | McKean et al. | |
| 5,554,169 A | 9/1996 | Green et al. | |
| 5,562,241 A | 10/1996 | Knodel et al. | |
| 5,562,682 A | 10/1996 | Oberlin et al. | |
| 5,564,615 A | 10/1996 | Bishop et al. | |
| 5,571,116 A | 11/1996 | Bolanos et al. | |
| 5,575,799 A | 11/1996 | Bolanos et al. | |
| 5,577,654 A | 11/1996 | Bishop | |
| 5,582,617 A | 12/1996 | Klieman et al. | |
| 5,584,425 A | 12/1996 | Savage et al. | |
| 5,586,711 A | 12/1996 | Plyley et al. | |
| 5,588,579 A | 12/1996 | Schnut et al. | |
| 5,601,224 A | 2/1997 | Bishop et al. | |
| 5,603,443 A | 2/1997 | Clark et al. | |
| 5,607,094 A | 3/1997 | Clark et al. | |
| 5,609,285 A | 3/1997 | Grant et al. | |
| 5,624,452 A | 4/1997 | Yates | |
| 5,626,595 A | 5/1997 | Sklar et al. | |
| 5,628,446 A | 5/1997 | Geiste et al. | |
| 5,630,539 A | 5/1997 | Plyley et al. | |
| 5,632,432 A | 5/1997 | Schulze et al. | |
| 5,636,779 A | 6/1997 | Palmer | |
| 5,639,008 A | 6/1997 | Gallagher et al. | |
| 5,649,937 A | 7/1997 | Bito et al. | |
| 5,651,491 A | 7/1997 | Heaton et al. | |
| 5,653,373 A | 8/1997 | Green et al. | |
| 5,653,374 A | 8/1997 | Young et al. | |
| 5,662,258 A | 9/1997 | Knodel et al. | |
| 5,667,517 A | 9/1997 | Hooven | |
| 5,667,527 A | 9/1997 | Cook | |
| 5,673,840 A | 10/1997 | Schulze et al. | |
| 5,673,841 A | 10/1997 | Schulze et al. | |
| 5,673,842 A | 10/1997 | Bittner et al. | |
| 5,678,748 A | 10/1997 | Plyley et al. | |
| 5,680,981 A | 10/1997 | Mililli et al. | |
| 5,680,982 A | 10/1997 | Schulze et al. | |
| 5,680,983 A | 10/1997 | Plyley et al. | |
| 5,688,270 A | 11/1997 | Yates et al. | |
| 5,692,668 A | 12/1997 | Schulze et al. | |
| 5,700,270 A | 12/1997 | Peyser et al. | |
| 5,702,408 A | 12/1997 | Wales et al. | |
| 5,704,534 A | 1/1998 | Huitema et al. | |
| 5,709,680 A | 1/1998 | Yates et al. | |
| 5,711,472 A | 1/1998 | Bryan | |
| 5,713,505 A | 2/1998 | Huitema | |
| 5,715,987 A | 2/1998 | Kelley et al. | |
| 5,715,988 A | 2/1998 | Palmer | |
| 5,716,366 A | 2/1998 | Yates | |
| 5,718,359 A | 2/1998 | Palmer et al. | |
| 5,725,536 A | 3/1998 | Oberlin et al. | |
| 5,725,554 A | 3/1998 | Simon et al. | |
| 5,730,758 A | 3/1998 | Allgeyer | |
| 5,732,871 A | 3/1998 | Clark et al. | |
| 5,735,445 A | 4/1998 | Vidal et al. | |
| 5,752,644 A | 5/1998 | Bolanos et al. | |
| 5,758,814 A | 6/1998 | Gallagher et al. | |
| 5,762,256 A | 6/1998 | Mastri et al. | |
| 5,779,130 A | 7/1998 | Alesi et al. | |
| 5,782,396 A | 7/1998 | Mastri et al. | |
| 5,792,165 A | 8/1998 | Klieman et al. | |
| 5,797,536 A | 8/1998 | Smith et al. | |
| 5,797,537 A | 8/1998 | Oberlin et al. | |
| 5,797,538 A | 8/1998 | Heaton et al. | |
| 5,823,066 A | 10/1998 | Huitema et al. | |
| 5,826,776 A | 10/1998 | Schulze et al. | |
| 5,833,690 A | 11/1998 | Yates et al. | |
| 5,833,695 A | 11/1998 | Yoon | |
| 5,836,503 A | 11/1998 | Ehrenfels et al. | |
| 5,836,960 A | 11/1998 | Kolesa et al. | |
| 5,839,639 A | 11/1998 | Sauer et al. | |
| 5,843,169 A * | 12/1998 | Taheri | 623/1.11 |

| | | | | | | |
|---|---|---|---|---|---|---|
| 5,865,361 | A | 2/1999 | Milliman et al. | 6,786,382 B1 * | 9/2004 | Hoffman ................. 227/178.1 |
| 5,868,760 | A | 2/1999 | McGuckin, Jr. | 6,793,652 B1 | 9/2004 | Whitman et al. |
| 5,871,135 | A | 2/1999 | Williamson, IV et al. | 6,805,273 B2 | 10/2004 | Bilotti et al. |
| 5,878,938 | A | 3/1999 | Bittner et al. | 6,817,509 B2 | 11/2004 | Geiste et al. |
| 5,893,506 | A | 4/1999 | Powell | 6,830,174 B2 | 12/2004 | Hillstead et al. |
| 5,894,979 | A | 4/1999 | Powell | 6,835,199 B2 | 12/2004 | McGuckin, Jr. et al. |
| 5,897,562 | A | 4/1999 | Bolanos et al. | 6,846,307 B2 | 1/2005 | Whitman et al. |
| 5,899,914 | A | 5/1999 | Zirps et al. | 6,846,308 B2 | 1/2005 | Whitman et al. |
| 5,906,625 | A | 5/1999 | Bito et al. | 6,846,309 B2 | 1/2005 | Whitman et al. |
| 5,908,427 | A | 6/1999 | McKean et al. | 6,849,071 B2 | 2/2005 | Whitman et al. |
| 5,911,353 | A | 6/1999 | Bolanos et al. | RE38,708 E | 3/2005 | Bolanos et al. |
| 5,918,791 | A | 7/1999 | Sorrentino et al. | 6,877,647 B2 | 4/2005 | Green et al. |
| 5,919,198 | A | 7/1999 | Graves, Jr. et al. | 6,905,057 B2 | 6/2005 | Swayze et al. |
| 5,931,847 | A | 8/1999 | Bittner et al. | 6,945,444 B2 | 9/2005 | Gresham et al. |
| 5,938,667 | A | 8/1999 | Peyser et al. | 6,953,138 B1 | 10/2005 | Dworak et al. |
| 5,941,442 | A | 8/1999 | Geiste et al. | 6,953,139 B2 | 10/2005 | Milliman et al. |
| 5,954,259 | A | 9/1999 | Viola et al. | 6,964,363 B2 * | 11/2005 | Wales et al. ............... 227/175.1 |
| 5,988,479 | A | 11/1999 | Palmer | 6,978,921 B2 | 12/2005 | Shelton, IV et al. |
| 6,010,054 | A | 1/2000 | Johnson et al. | 6,978,922 B2 | 12/2005 | Bilotti et al. |
| 6,017,356 | A | 1/2000 | Frederick et al. | 6,981,628 B2 | 1/2006 | Wales |
| 6,022,352 | A | 2/2000 | Vandewalle | 6,981,941 B2 | 1/2006 | Whitman et al. |
| 6,032,849 | A | 3/2000 | Mastri et al. | 6,988,649 B2 | 1/2006 | Shelton, IV et al. |
| 6,033,427 | A | 3/2000 | Lee | 7,000,818 B2 | 2/2006 | Shelton, IV et al. |
| 6,045,560 | A | 4/2000 | McKean et al. | 7,008,435 B2 | 3/2006 | Cummins |
| 6,077,286 | A | 6/2000 | Cuschieri et al. | 7,018,390 B2 | 3/2006 | Turovskiy et al. |
| 6,079,606 | A | 6/2000 | Milliman et al. | 7,032,798 B2 | 4/2006 | Whitman et al. |
| 6,083,234 | A | 7/2000 | Nicholas et al. | 7,032,799 B2 | 4/2006 | Viola et al. |
| 6,083,242 | A | 7/2000 | Cook | 7,044,352 B2 | 5/2006 | Shelton, IV et al. |
| 6,086,600 | A | 7/2000 | Kortenbach | 7,055,730 B2 | 6/2006 | Ehrenfels et al. |
| 6,099,551 | A | 8/2000 | Gabbay | 7,055,731 B2 | 6/2006 | Shelton, IV et al. |
| 6,102,271 | A | 8/2000 | Longo et al. | 7,056,330 B2 | 6/2006 | Gayton |
| 6,109,500 | A | 8/2000 | Alli et al. | 7,066,944 B2 | 6/2006 | Laufer et al. |
| H1904 | H | 10/2000 | Yates et al. | 7,077,856 B2 | 7/2006 | Whitman |
| 6,126,058 | A | 10/2000 | Adams et al. | 7,083,075 B2 | 8/2006 | Swayze et al. |
| 6,131,789 | A | 10/2000 | Schulze et al. | 7,090,684 B2 | 8/2006 | McGuckin, Jr. et al. |
| 6,155,473 | A | 12/2000 | Tompkins et al. | 7,114,642 B2 | 10/2006 | Whitman |
| 6,171,330 | B1 | 1/2001 | Benchetrit | 7,118,582 B1 | 10/2006 | Wang et al. |
| 6,202,914 | B1 | 3/2001 | Geiste et al. | 7,140,527 B2 | 11/2006 | Ehrenfels et al. |
| 6,241,139 | B1 | 6/2001 | Milliman et al. | 7,159,750 B2 | 1/2007 | Racenet et al. |
| 6,250,532 | B1 | 6/2001 | Green et al. | 7,188,758 B2 | 3/2007 | Viola et al. |
| 6,264,086 | B1 | 7/2001 | McGuckin, Jr. | 7,210,609 B2 | 5/2007 | Leiboff et |
| 6,264,087 | B1 | 7/2001 | Whitman | 7,235,089 B1 | 6/2007 | McGuckin, Jr. |
| 6,273,897 | B1 | 8/2001 | Dalessandro et al. | 7,238,195 B2 | 7/2007 | Viola |
| 6,315,184 | B1 | 11/2001 | Whitman | 7,246,734 B2 | 7/2007 | Shelton, IV |
| 6,320,123 | B1 | 11/2001 | Reimers | 7,278,563 B1 | 10/2007 | Green |
| 6,358,224 | B1 | 3/2002 | Tims et al. | 7,297,149 B2 | 11/2007 | Vitali et al. |
| 6,387,113 | B1 | 5/2002 | Hawkins et al. | 7,303,106 B2 | 12/2007 | Milliman et al. |
| 6,416,486 | B1 | 7/2002 | Wampler | 7,328,828 B2 | 2/2008 | Ortiz et al. |
| RE37,814 | E | 8/2002 | Allgeyer | 7,380,695 B2 | 6/2008 | Doll et al. |
| 6,436,107 | B1 | 8/2002 | Wang et al. | 7,380,696 B2 | 6/2008 | Shelton, IV et al. |
| 6,443,973 | B1 | 9/2002 | Whitman | 7,404,508 B2 | 7/2008 | Smith et al. |
| 6,488,197 | B1 | 12/2002 | Whitman | 7,407,075 B2 | 8/2008 | Holsten et al. |
| 6,491,201 | B1 | 12/2002 | Whitman | 7,407,078 B2 | 8/2008 | Shelton, IV et al. |
| 6,494,896 | B1 | 12/2002 | D'Alessio et al. | 7,416,101 B2 | 8/2008 | Shelton, IV et al. |
| 6,505,768 | B2 | 1/2003 | Whitman | 7,422,136 B1 | 9/2008 | Marczyk |
| 6,517,565 | B1 | 2/2003 | Whitman et al. | 7,424,965 B2 | 9/2008 | Racenet et al. |
| 6,522,101 | B2 | 2/2003 | Malackowski | 7,431,188 B1 | 10/2008 | Marczyk |
| 6,569,171 | B2 | 5/2003 | DeGuillebon et al. | 7,431,189 B2 | 10/2008 | Shelton, IV et al. |
| 6,601,749 | B2 | 8/2003 | Sullivan et al. | 7,431,730 B2 | 10/2008 | Viola |
| 6,616,686 | B2 | 9/2003 | Coleman et al. | 7,434,717 B2 | 10/2008 | Shelton, IV et al. |
| 6,619,529 | B2 | 9/2003 | Green et al. | 7,438,209 B1 | 10/2008 | Hess et al. |
| 6,629,988 | B2 | 10/2003 | Weadock | 7,441,684 B2 | 10/2008 | Shelton, IV et al. |
| RE38,335 | E | 11/2003 | Aust et al. | 7,441,685 B1 | 10/2008 | Boudreaux |
| 6,644,532 | B2 | 11/2003 | Green et al. | 7,448,525 B2 | 11/2008 | Shelton, IV et al. |
| 6,669,073 | B2 | 12/2003 | Milliman et al. | 7,481,347 B2 | 1/2009 | Roy |
| 6,681,979 | B2 | 1/2004 | Whitman | 7,490,749 B2 | 2/2009 | Schall et al. |
| 6,695,199 | B2 | 2/2004 | Whitman | 7,494,039 B2 | 2/2009 | Racenet et al. |
| 6,698,643 | B2 | 3/2004 | Whitman | 7,500,979 B2 | 3/2009 | Hueil et al. |
| 6,716,233 | B1 | 4/2004 | Whitman | 7,506,791 B2 | 3/2009 | Omaits et al. |
| 6,752,816 | B2 | 6/2004 | Culp et al. | 7,546,940 B2 | 6/2009 | Milliman et al. |
| 6,755,338 | B2 | 6/2004 | Hahnen et al. | 2002/0062136 A1 * | 5/2002 | Hillstead et al. ............ 606/205 |
| 6,767,356 | B2 | 7/2004 | Kanner et al. | 2003/0093103 A1 | 5/2003 | Malackowski et al. |
| 6,773,438 | B1 | 8/2004 | Knodel et al. | 2003/0105478 A1 | 6/2003 | Whitman et al. |

| | | | | | |
|---|---|---|---|---|---|
| 2003/0130677 A1 | 7/2003 | Whitman et al. | 2007/0175955 A1 | 8/2007 | Shelton, IV et al. |
| 2003/0216778 A1 | 11/2003 | Weadock | 2007/0175956 A1 | 8/2007 | Swayze et al. |
| 2004/0006372 A1 | 1/2004 | Racenet et al. | 2007/0175957 A1 | 8/2007 | Shelton, IV et al. |
| 2004/0028502 A1 | 2/2004 | Cummins | 2007/0175958 A1 | 8/2007 | Shelton, IV et al. |
| 2004/0034369 A1 | 2/2004 | Sauer et al. | 2007/0175959 A1 | 8/2007 | Shelton, IV et al. |
| 2004/0044364 A1 | 3/2004 | DeVries et al. | 2007/0175960 A1 | 8/2007 | Shelton, IV et al. |
| 2004/0094597 A1 | 5/2004 | Whitman et al. | 2007/0175961 A1 | 8/2007 | Shelton, IV et al. |
| 2004/0097987 A1 | 5/2004 | Pugsley et al. | 2007/0175962 A1 | 8/2007 | Shelton, IV et al. |
| 2004/0111081 A1 | 6/2004 | Whitman et al. | 2007/0175964 A1 | 8/2007 | Shelton, IV et al. |
| 2004/0122471 A1 | 6/2004 | Toby et al. | 2007/0179476 A1 | 8/2007 | Shelton, IV et al. |
| 2004/0167572 A1 | 8/2004 | Roth et al. | 2007/0194079 A1 | 8/2007 | Hueil et al. |
| 2004/0222268 A1 | 11/2004 | Bilotti et al. | 2007/0194080 A1 | 8/2007 | Swayze et al. |
| 2004/0232199 A1 | 11/2004 | Shelton, IV et al. | 2007/0194081 A1 | 8/2007 | Hueil et al. |
| 2004/0243151 A1 | 12/2004 | Demmy et al. | 2007/0194082 A1 | 8/2007 | Morgan et al. |
| 2004/0243176 A1 | 12/2004 | Hahnen et al. | 2007/0233053 A1 | 10/2007 | Shelton, IV et al. |
| 2004/0254608 A1 | 12/2004 | Huitema et al. | 2007/0246505 A1 | 10/2007 | Pace-Floridia et al. |
| 2005/0006434 A1 | 1/2005 | Wales et al. | 2007/0295780 A1 | 12/2007 | Shelton et al. |
| 2005/0021026 A1 | 1/2005 | Baily | 2008/0029570 A1 | 2/2008 | Shelton et al. |
| 2005/0059997 A1 | 3/2005 | Bauman et al. | 2008/0029573 A1 | 2/2008 | Shelton et al. |
| 2005/0070958 A1 | 3/2005 | Swayze et al. | 2008/0029574 A1 | 2/2008 | Shelton et al. |
| 2005/0072827 A1 | 4/2005 | Mollenauer | 2008/0029575 A1 | 2/2008 | Shelton et al. |
| 2005/0103819 A1 | 5/2005 | Racenet et al. | 2008/0029576 A1 | 2/2008 | Shelton et al. |
| 2005/0107824 A1 | 5/2005 | Hillstead et al. | 2008/0078800 A1 | 4/2008 | Hess et al. |
| 2005/0119669 A1 | 6/2005 | Demmy | 2008/0078801 A1 | 4/2008 | Shelton et al. |
| 2005/0125009 A1 | 6/2005 | Perry et al. | 2008/0078802 A1 | 4/2008 | Hess et al. |
| 2005/0131390 A1 | 6/2005 | Heinrich et al. | 2008/0078803 A1 | 4/2008 | Shelton et al. |
| 2005/0143759 A1 | 6/2005 | Kelly | 2008/0078804 A1 | 4/2008 | Shelton et al. |
| 2005/0165415 A1 | 7/2005 | Wales | 2008/0078806 A1 | 4/2008 | Omaits et al. |
| 2005/0173490 A1 | 8/2005 | Shelton, IV | 2008/0078807 A1 | 4/2008 | Hess et al. |
| 2005/0184121 A1 | 8/2005 | Heinrich | 2008/0078808 A1 | 4/2008 | Hess et al. |
| 2005/0187576 A1 | 8/2005 | Whitman et al. | 2008/0082115 A1 | 4/2008 | Morgan et al. |
| 2005/0192609 A1 | 9/2005 | Whitman et al. | 2008/0082124 A1 | 4/2008 | Hess et al. |
| 2005/0203550 A1 | 9/2005 | Laufer et al. | 2008/0082125 A1 | 4/2008 | Murray et al. |
| 2005/0216055 A1 | 9/2005 | Scirica et al. | 2008/0082126 A1 | 4/2008 | Murray et al. |
| 2005/0230453 A1 | 10/2005 | Viola | 2008/0164296 A1 | 7/2008 | Shelton et al. |
| 2005/0263562 A1 | 12/2005 | Shelton et al. | 2008/0167522 A1 | 7/2008 | Giordano et al. |
| 2005/0274768 A1 | 12/2005 | Cummins et al. | 2008/0167644 A1 | 7/2008 | Shelton et al. |
| 2006/0011699 A1 | 1/2006 | Olson et al. | 2008/0167670 A1 | 7/2008 | Shelton et al. |
| 2006/0025813 A1 | 2/2006 | Shelton et al. | 2008/0167671 A1 | 7/2008 | Giordano et al. |
| 2006/0025816 A1 | 2/2006 | Shelton | 2008/0167672 A1 | 7/2008 | Giordano et al. |
| 2006/0047307 A1 | 3/2006 | Ortiz et al. | 2008/0167736 A1 | 7/2008 | Swayze et al. |
| 2006/0047308 A1 | 3/2006 | Ortiz et al. | 2008/0169328 A1 | 7/2008 | Shelton |
| 2006/0049229 A1 | 3/2006 | Milliman et al. | 2008/0169329 A1 | 7/2008 | Shelton et al. |
| 2006/0052825 A1 | 3/2006 | Ransick et al. | 2008/0169330 A1 | 7/2008 | Shelton et al. |
| 2006/0085033 A1 | 4/2006 | Criscuolo et al. | 2008/0169331 A1 | 7/2008 | Shelton et al. |
| 2006/0100643 A1 | 5/2006 | Laufer et al. | 2008/0169332 A1 | 7/2008 | Shelton et al. |
| 2006/0122636 A1 | 6/2006 | Bailly et al. | 2008/0169333 A1 | 7/2008 | Shelton et al. |
| 2006/0142772 A1 | 6/2006 | Ralph et al. | 2008/0210738 A1 | 9/2008 | Shelton et al. |
| 2006/0151567 A1 | 7/2006 | Roy | 2008/0237296 A1 | 10/2008 | Boudreaux et al. |
| 2006/0190028 A1 | 8/2006 | Wales et al. | 2008/0296343 A1 | 12/2008 | Schall et al. |
| 2006/0226196 A1 | 10/2006 | Hueil et al. | 2008/0296345 A1 | 12/2008 | Shelton, IV et al. |
| 2006/0241655 A1* | 10/2006 | Viola .................. 606/142 | 2008/0296346 A1 | 12/2008 | Shelton, IV et al. |
| 2006/0241692 A1 | 10/2006 | McGuckin, Jr. et al. | 2008/0296347 A1 | 12/2008 | Shelton, IV et al. |
| 2006/0273135 A1 | 12/2006 | Beetel | 2008/0300579 A1 | 12/2008 | Broehl et al. |
| 2006/0289602 A1 | 12/2006 | Wales et al. | 2008/0300580 A1 | 12/2008 | Shelton, IV et al. |
| 2007/0023477 A1 | 2/2007 | Whitman et al. | 2008/0300613 A1 | 12/2008 | Shelton, IV et al. |
| 2007/0045379 A1 | 3/2007 | Shelton, IV | 2008/0308601 A1 | 12/2008 | Timm et al. |
| 2007/0073340 A1 | 3/2007 | Shelton, IV et al. | 2008/0308602 A1 | 12/2008 | Timm et al. |
| 2007/0075114 A1 | 4/2007 | Shelton, IV et al. | 2008/0308603 A1 | 12/2008 | Shelton, IV et al. |
| 2007/0083234 A1 | 4/2007 | Shelton, IV et al. | 2008/0308604 A1 | 12/2008 | Timm et al. |
| 2007/0102452 A1 | 5/2007 | Shelton, IV et al. | 2008/0308606 A1 | 12/2008 | Timm et al. |
| 2007/0102453 A1 | 5/2007 | Morgan et al. | 2008/0308607 A1 | 12/2008 | Timm et al. |
| 2007/0102472 A1 | 5/2007 | Shelton, IV | 2008/0314954 A1 | 12/2008 | Boudreaux |
| 2007/0102474 A1 | 5/2007 | Shelton, IV et al. | 2008/0314955 A1 | 12/2008 | Boudreaux et al. |
| 2007/0102476 A1 | 5/2007 | Shelton, IV et al. | 2008/0314956 A1 | 12/2008 | Boudreaux |
| 2007/0106317 A1 | 5/2007 | Shelton, IV et al. | 2008/0314957 A1 | 12/2008 | Boudreaux |
| 2007/0114261 A1 | 5/2007 | Ortiz et al. | 2008/0314960 A1 | 12/2008 | Marczyk et al. |
| 2007/0158385 A1 | 7/2007 | Hueil et al. | 2008/0314961 A1 | 12/2008 | Boudreaux et al. |
| 2007/0170225 A1 | 7/2007 | Shelton, IV et al. | 2008/0314962 A1 | 12/2008 | Boudreaux |
| 2007/0175949 A1 | 8/2007 | Shelton, IV et al. | 2009/0001121 A1 | 1/2009 | Hess et al. |
| 2007/0175950 A1 | 8/2007 | Shelton, IV et al. | 2009/0001123 A1 | 1/2009 | Morgan et al. |
| 2007/0175951 A1 | 8/2007 | Shelton, IV et al. | 2009/0001124 A1 | 1/2009 | Hess et al. |
| 2007/0175953 A1 | 8/2007 | Shelton, IV et al. | 2009/0001125 A1 | 1/2009 | Hess et al. |

| | | | | | | |
|---|---|---|---|---|---|---|
| 2009/0001126 | A1 | 1/2009 | Hess et al. | EP | 0578425 B1 | 9/1997 |
| 2009/0001128 | A1 | 1/2009 | Weisenburgh, II et al. | EP | 0625335 B1 | 11/1997 |
| 2009/0001130 | A1 | 1/2009 | Hess et al. | EP | 0552423 B1 | 1/1998 |
| 2009/0005807 | A1 | 1/2009 | Hess et al. | EP | 0592244 B1 | 1/1998 |
| 2009/0005808 | A1 | 1/2009 | Hess et al. | EP | 0648476 B1 | 1/1998 |
| 2009/0005809 | A1 | 1/2009 | Hess et al. | EP | 0676173 B1 | 9/1998 |
| 2009/0012556 | A1 | 1/2009 | Boudreaux et al. | EP | 0603472 B1 | 11/1998 |
| 2009/0076534 | A1 | 3/2009 | Shelton, IV et al. | EP | 0605351 B1 | 11/1998 |
| 2009/0200355 | A1 | 8/2009 | Baxter, III et al. | EP | 0878169 A1 | 11/1998 |
| 2009/0206123 | A1 | 8/2009 | Doll et al. | EP | 0879742 A1 | 11/1998 |
| 2009/0206124 | A1 | 8/2009 | Hall et al. | EP | 0760230 B1 | 2/1999 |
| 2009/0206125 | A1 | 8/2009 | Huitema et al. | EP | 0537572 B1 | 6/1999 |
| 2009/0206126 | A1 | 8/2009 | Huitema et al. | EP | 0552050 B1 | 5/2000 |
| 2009/0206128 | A1 | 8/2009 | Hueil et al. | EP | 1090592 A1 | 4/2001 |
| 2009/0206129 | A1 | 8/2009 | Doll et al. | EP | 1256318 B1 | 5/2001 |
| 2009/0206130 | A1 | 8/2009 | Hall et al. | EP | 0908152 B1 | 1/2002 |
| 2009/0206131 | A1 | 8/2009 | Weisenburgh, II et al. | EP | 0872213 B1 | 5/2002 |
| 2009/0206132 | A1 | 8/2009 | Hueil et al. | EP | 1238634 A2 | 9/2002 |
| 2009/0206133 | A1 | 8/2009 | Morgan et al. | EP | 0656188 B1 | 1/2003 |
| 2009/0206134 | A1 | 8/2009 | Swayze et al. | EP | 0829235 B1 | 6/2003 |
| 2009/0206135 | A1 | 8/2009 | Hall et al. | EP | 0813843 B1 | 10/2003 |
| 2009/0206136 | A1 | 8/2009 | Moore et al. | EP | 0741996 B1 | 2/2004 |
| 2009/0206137 | A1 | 8/2009 | Hall et al. | EP | 0705570 B1 | 4/2004 |
| 2009/0206138 | A1 | 8/2009 | Smith et al. | EP | 1086713 B1 | 5/2004 |
| 2009/0206139 | A1 | 8/2009 | Hall et al. | EP | 1426012 A1 | 6/2004 |
| 2009/0206140 | A1 | 8/2009 | Scheib et al. | EP | 0888749 B1 | 9/2004 |
| 2009/0206141 | A1 | 8/2009 | Huitema et al. | EP | 1477119 A1 | 11/2004 |
| 2009/0206142 | A1 | 8/2009 | Huitema et al. | EP | 1479345 A1 | 11/2004 |
| 2009/0206143 | A1 | 8/2009 | Huitema et al. | EP | 1479347 A1 | 11/2004 |
| 2009/0206144 | A1 | 8/2009 | Doll et al. | EP | 1479348 A1 | 11/2004 |
| 2009/0209946 | A1 | 8/2009 | Swayze et al. | EP | 1520521 A1 | 4/2005 |
| 2009/0255975 | A1 | 10/2009 | Zemlok et al. | EP | 1520523 A1 | 4/2005 |
| 2009/0255976 | A1 | 10/2009 | Marczyk et al. | EP | 1520525 A1 | 4/2005 |
| 2009/0255977 | A1 | 10/2009 | Zemlok | EP | 1522264 A1 | 4/2005 |
| 2009/0255978 | A1 | 10/2009 | Viola et al. | EP | 1550408 A1 | 7/2005 |
| 2009/0289096 | A1 | 11/2009 | Shelton, Iv et al. | EP | 1557129 A1 | 7/2005 |
| | | | | EP | 1064883 B1 | 8/2005 |

FOREIGN PATENT DOCUMENTS

| | | | | | |
|---|---|---|---|---|---|
| | | | EP | 1157666 B1 | 9/2005 |
| CA | 2512960 | A1 | 1/2006 | EP | 1621138 A2 | 2/2006 |
| CA | 2514274 | A1 | 1/2006 | EP | 1621139 A2 | 2/2006 |
| DE | 273689 | C | 5/1914 | EP | 1621141 A2 | 2/2006 |
| DE | 1775926 | A | 1/1972 | EP | 1621145 A2 | 2/2006 |
| DE | 9412228 | U | 9/1994 | EP | 1652481 A2 | 5/2006 |
| DE | 19924311 | A1 | 11/2000 | EP | 1382303 B1 | 6/2006 |
| DE | 69328576 | T2 | 1/2001 | EP | 1045672 B1 | 8/2006 |
| DE | 20112837 | U1 | 10/2001 | EP | 1617768 B1 | 8/2006 |
| DE | 20121753 | U1 | 4/2003 | EP | 1702567 A2 | 9/2006 |
| DE | 10314072 | A1 | 10/2004 | EP | 1129665 B1 | 11/2006 |
| EP | 0122046 | A1 | 10/1984 | EP | 1256317 B1 | 12/2006 |
| EP | 0033548 | B1 | 5/1986 | EP | 1728473 A1 | 12/2006 |
| EP | 0276104 | A2 | 7/1988 | EP | 1728475 A2 | 12/2006 |
| EP | 0639349 | A2 | 2/1994 | EP | 1479346 B1 | 1/2007 |
| EP | 0324636 | B1 | 3/1994 | EP | 1484024 B1 | 1/2007 |
| EP | 0593920 | A1 | 4/1994 | EP | 1754445 A2 | 2/2007 |
| EP | 0600182 | A2 | 6/1994 | EP | 1759812 A1 | 3/2007 |
| EP | 0630612 | A1 | 12/1994 | EP | 1769756 A1 | 4/2007 |
| EP | 0634144 | A1 | 1/1995 | EP | 1769758 A1 | 4/2007 |
| EP | 0646356 | A2 | 4/1995 | EP | 1785097 A2 | 5/2007 |
| EP | 0646357 | A1 | 4/1995 | EP | 1790293 A2 | 5/2007 |
| EP | 0653189 | A2 | 5/1995 | EP | 1300117 B1 | 8/2007 |
| EP | 0669104 | A1 | 8/1995 | EP | 1813199 A1 | 8/2007 |
| EP | 0679367 | A2 | 11/1995 | EP | 1813201 A1 | 8/2007 |
| EP | 0392547 | B1 | 12/1995 | EP | 1813203 A2 | 8/2007 |
| EP | 0685204 | A1 | 12/1995 | EP | 1813207 A1 | 8/2007 |
| EP | 0699418 | A1 | 3/1996 | EP | 1813209 A1 | 8/2007 |
| EP | 0702937 | A1 | 3/1996 | EP | 1872727 A1 | 1/2008 |
| EP | 0705571 | A1 | 4/1996 | EP | 1839596 A2 | 2/2008 |
| EP | 0484677 | B2 | 6/1996 | EP | 1897502 A1 | 3/2008 |
| EP | 0541987 | B1 | 7/1996 | EP | 1702568 B1 | 7/2008 |
| EP | 0667119 | B1 | 7/1996 | EP | 1759645 B1 | 11/2008 |
| EP | 0770355 | A1 | 5/1997 | EP | 1749486 B1 | 3/2009 |
| EP | 0503662 | B1 | 6/1997 | FR | 999646 | A | 2/1952 |
| | | | | FR | 1112936 | A | 3/1956 |

| | | | |
|---|---|---|---|
| FR | 2765794 A | 1/1999 | |
| GB | 939929 A | 10/1963 | |
| GB | 1210522 A | 10/1970 | |
| GB | 2336214 A | 10/1999 | |
| JP | 6007357 A | 1/1994 | |
| JP | 7051273 A | 2/1995 | |
| JP | 8033641 A | 2/1996 | |
| JP | 8229050 A | 9/1996 | |
| JP | 2000287987 A | 10/2000 | |
| JP | 2001286477 A | 10/2001 | |
| JP | 2002369820 A | 12/2002 | |
| JP | 2005505322 T | 2/2005 | |
| JP | 2005103293 A | 4/2005 | |
| RU | 2187249 C2 | 8/2002 | |
| RU | 2225170 C2 | 3/2004 | |
| SU | 1377053 A1 | 2/1988 | |
| SU | 1561964 A1 | 5/1990 | |
| SU | 1722476 A1 | 3/1992 | |
| WO | WO 93/08755 A1 | 5/1993 | |
| WO | WO 95/18572 A1 | 7/1995 | |
| WO | WO 95/23557 A1 | 9/1995 | |
| WO | WO 95/29639 A1 | 11/1995 | |
| WO | WO 96/35464 A1 | 11/1996 | |
| WO | WO 97/34533 A1 | 9/1997 | |
| WO | WO 97/39688 A2 | 10/1997 | |
| WO | WO 98/30153 A1 | 7/1998 | |
| WO | WO 99/12483 A1 | 3/1999 | |
| WO | WO 99/15086 A1 | 4/1999 | |
| WO | WO 99/34744 A1 | 7/1999 | |
| WO | WO 99/45849 A1 | 9/1999 | |
| WO | WO 00/24322 A1 | 5/2000 | |
| WO | WO 00/57796 A1 | 10/2000 | |
| WO | WO 00/64365 A1 | 11/2000 | |
| WO | WO 00/72762 A1 | 12/2000 | |
| WO | WO 00/72765 A1 | 12/2000 | |
| WO | WO 01/05702 A1 | 1/2001 | |
| WO | WO 01/10482 A1 | 2/2001 | |
| WO | WO 01/54594 A1 | 8/2001 | |
| WO | WO 01/62158 A2 | 8/2001 | |
| WO | WO 01/62162 A1 | 8/2001 | |
| WO | WO 01/62164 A2 | 8/2001 | |
| WO | WO 01/91646 A1 | 12/2001 | |
| WO | WO 02/07608 A2 | 1/2002 | |
| WO | WO 02/07618 A1 | 1/2002 | |
| WO | WO 02/17799 A1 | 3/2002 | |
| WO | WO 02/19920 A1 | 3/2002 | |
| WO | WO 02/30297 A2 | 4/2002 | |
| WO | WO 02/32322 A2 | 4/2002 | |
| WO | WO 02/043571 A2 | 6/2002 | |
| WO | WO 02/058568 A1 | 8/2002 | |
| WO | WO 02/067785 A2 | 9/2002 | |
| WO | WO 02/098302 A1 | 12/2002 | |
| WO | WO 03/000138 A2 | 1/2003 | |
| WO | WO 03/001329 A2 | 1/2003 | |
| WO | WO 03/013363 A1 | 2/2003 | |
| WO | WO 03/020106 A2 | 3/2003 | |
| WO | WO 03/079909 A3 | 3/2003 | |
| WO | WO 03/030743 A2 | 4/2003 | |
| WO | WO 03/037193 A1 | 5/2003 | |
| WO | WO 03/047436 A3 | 6/2003 | |
| WO | WO 03/057048 A1 | 7/2003 | |
| WO | WO 03/057058 A1 | 7/2003 | |
| WO | WO 03/063694 A1 | 8/2003 | |
| WO | WO 03/077769 A1 | 9/2003 | |
| WO | WO 03/082126 A1 | 10/2003 | |
| WO | WO 03/088845 A2 | 10/2003 | |
| WO | WO 03/090630 A2 | 11/2003 | |
| WO | WO 03/094743 A1 | 11/2003 | |
| WO | WO 03/094745 A1 | 11/2003 | |
| WO | WO 03/094746 A1 | 11/2003 | |
| WO | WO 03/094747 A1 | 11/2003 | |
| WO | WO 03/101313 A1 | 12/2003 | |
| WO | WO 03/105698 A2 | 12/2003 | |
| WO | WO 03/105702 A2 | 12/2003 | |
| WO | WO 2004/006980 A2 | 1/2004 | |
| WO | WO 2004/028585 A2 | 4/2004 | |
| WO | WO 2004/032754 A2 | 4/2004 | |
| WO | WO 2004/032760 A2 | 4/2004 | |
| WO | WO 2004/032762 A1 | 4/2004 | |
| WO | WO 2004/032763 A2 | 4/2004 | |
| WO | WO 2004/047653 A2 | 6/2004 | |
| WO | WO 2004/049956 A2 | 6/2004 | |
| WO | WO 2004/086987 A1 | 10/2004 | |
| WO | WO 2004/096057 A2 | 11/2004 | |
| WO | WO 2004/105621 A1 | 12/2004 | |
| WO | WO 2004/112618 A2 | 12/2004 | |
| WO | WO 2004/112652 A2 | 12/2004 | |
| WO | WO 2005/027983 A2 | 3/2005 | |
| WO | WO 2005/037329 A2 | 4/2005 | |
| WO | WO 2005/078892 A1 | 8/2005 | |
| WO | WO 2005/096954 A2 | 10/2005 | |
| WO | WO 2005/112808 A1 | 12/2005 | |
| WO | WO 2005/115251 A2 | 12/2005 | |
| WO | WO 2006/044490 A2 | 4/2006 | |
| WO | WO 2006/044581 A2 | 4/2006 | |
| WO | WO 2006/044810 A2 | 4/2006 | |
| WO | WO 2006/083748 A1 | 8/2006 | |
| WO | WO 2006/115958 A1 | 11/2006 | |
| WO | WO 2006/132992 A1 | 12/2006 | |
| WO | WO 2007/016290 A2 | 2/2007 | |
| WO | WO 2007/018898 A2 | 2/2007 | |
| WO | WO 2007/121579 A1 | 11/2007 | |
| WO | WO 2007/139734 A2 | 12/2007 | |
| WO | WO 2007/142625 A2 | 12/2007 | |
| WO | WO 2008/039270 A1 | 4/2008 | |
| WO | WO 2008/045383 A2 | 4/2008 | |

OTHER PUBLICATIONS

Disclosed Anonymously, "Motor-Driven Surgical Stapler Improvements," Research Disclosure Database No. 526041, Published: Feb. 2008.

C.C. Thompson et al., "Peroral Endoscopic Reduction of Dilated Gastrojejunal Anastomosis After Roux-en-Y Gastric Bypass: A Possible New Option for Patients with Weight Regain," Surg Endosc (2006) vol. 20, pp. 1744-1748.

B.R. Coolman, DVM, MS et al., "Comparison of Skin Staples With Sutures for Anastomosis of the Small Intestine in Dogs," Abstract; http://www.blackwell-synergy.com/doi/abs/10.1053/jvet.2000.7539?cookieSet=1&journalCode=vsu which redirects to http://www3.interscience.wiley.com/journal/119040681/abstract?CRETRY=1&SRETRY=0; [online] accessed: Sep. 22, 2008 (2 pages).

European Search Opinion, Application No. 06255737.6, dated Jul. 10, 2009 (7 pages).

* cited by examiner

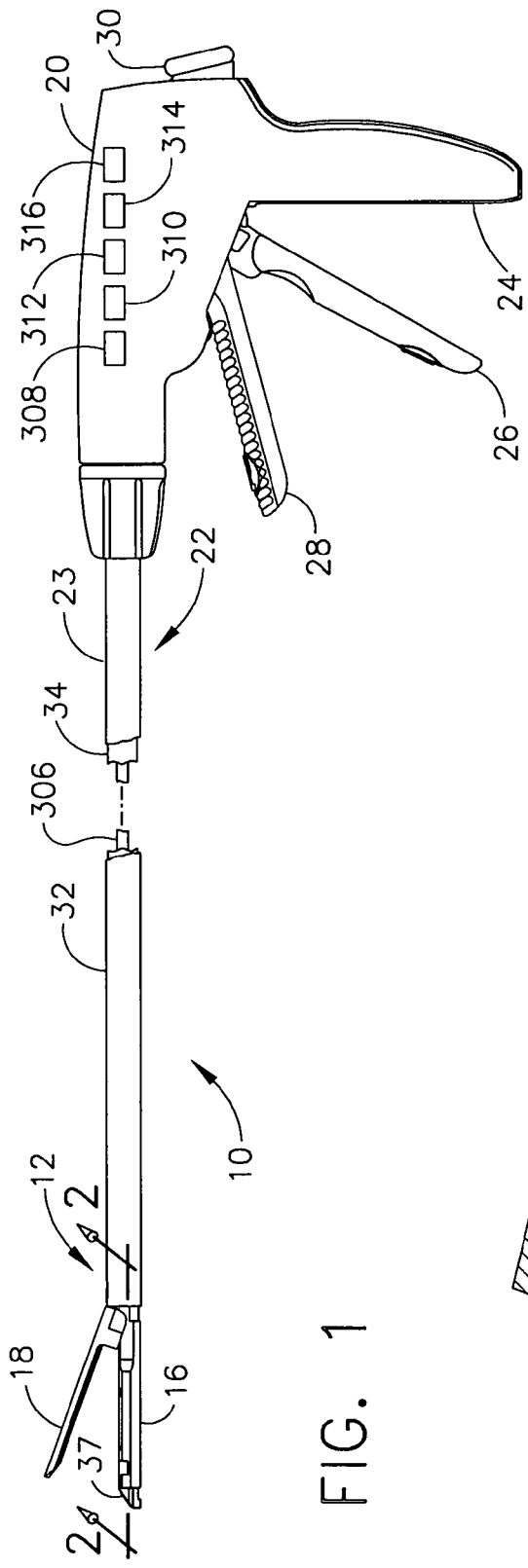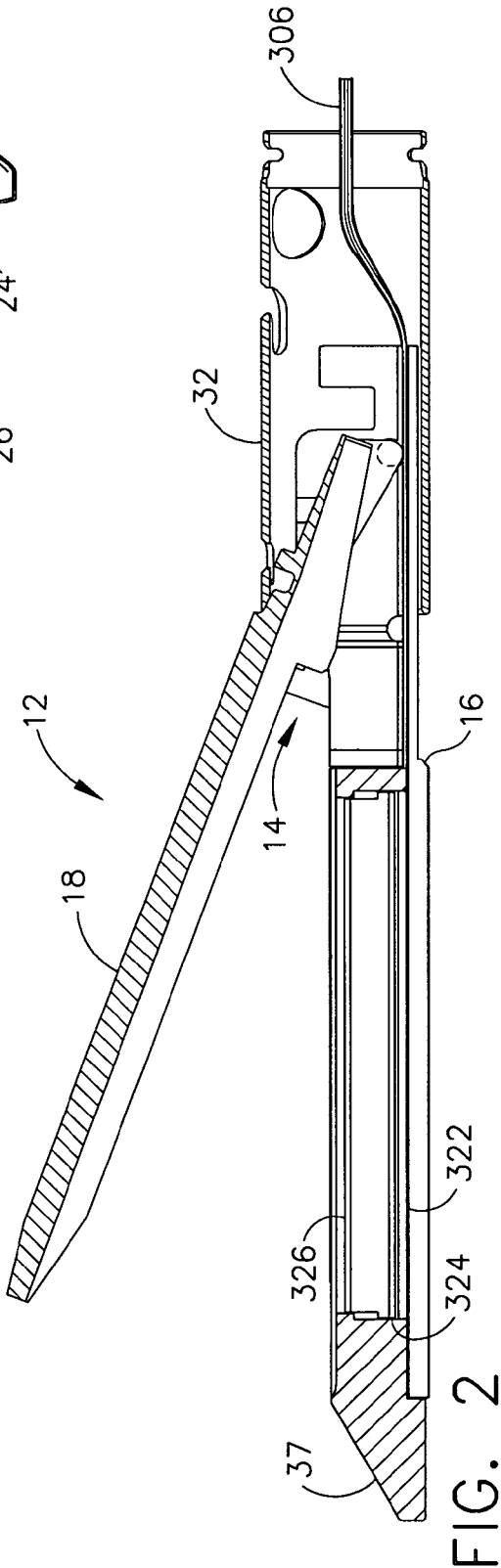

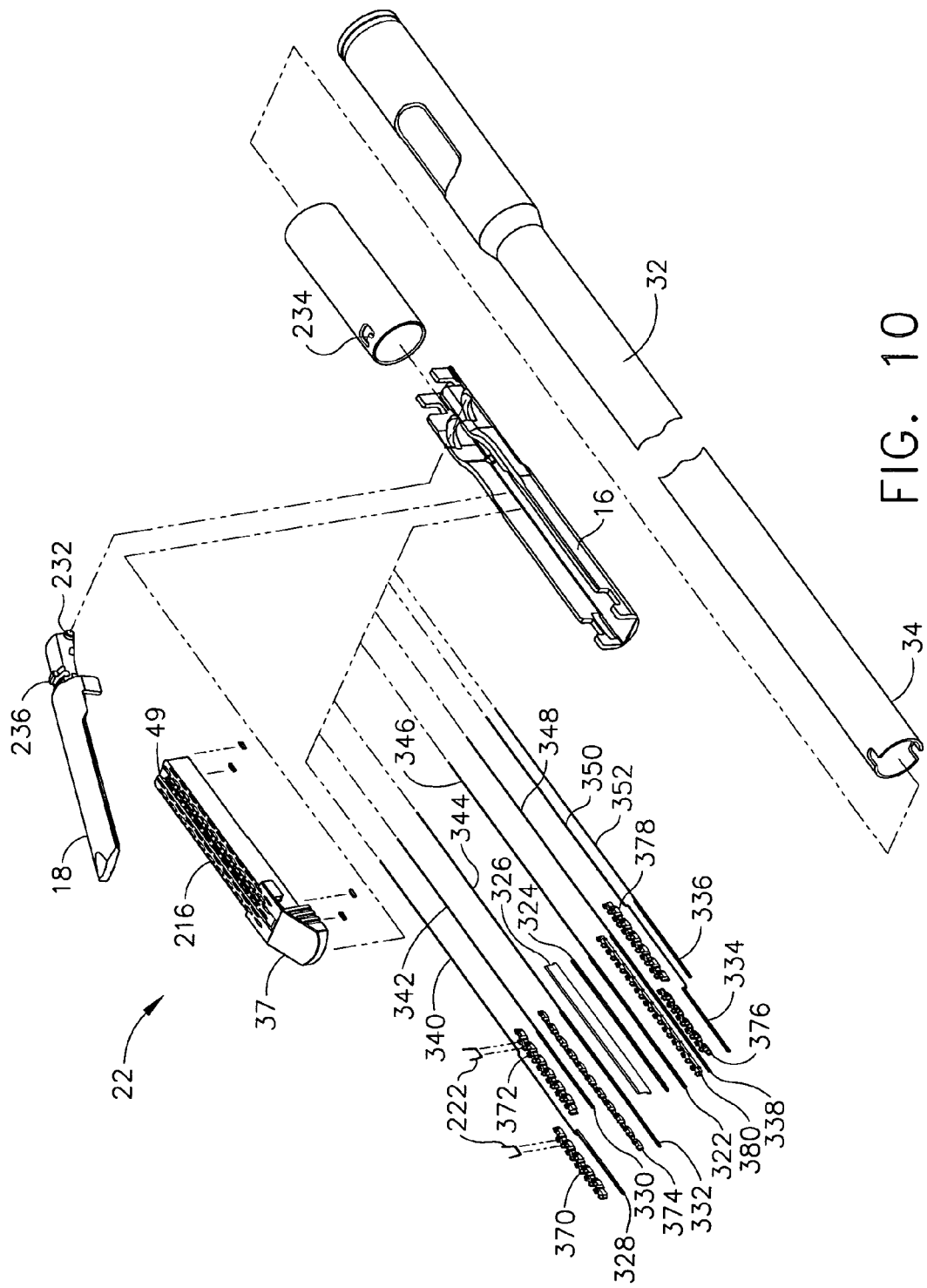

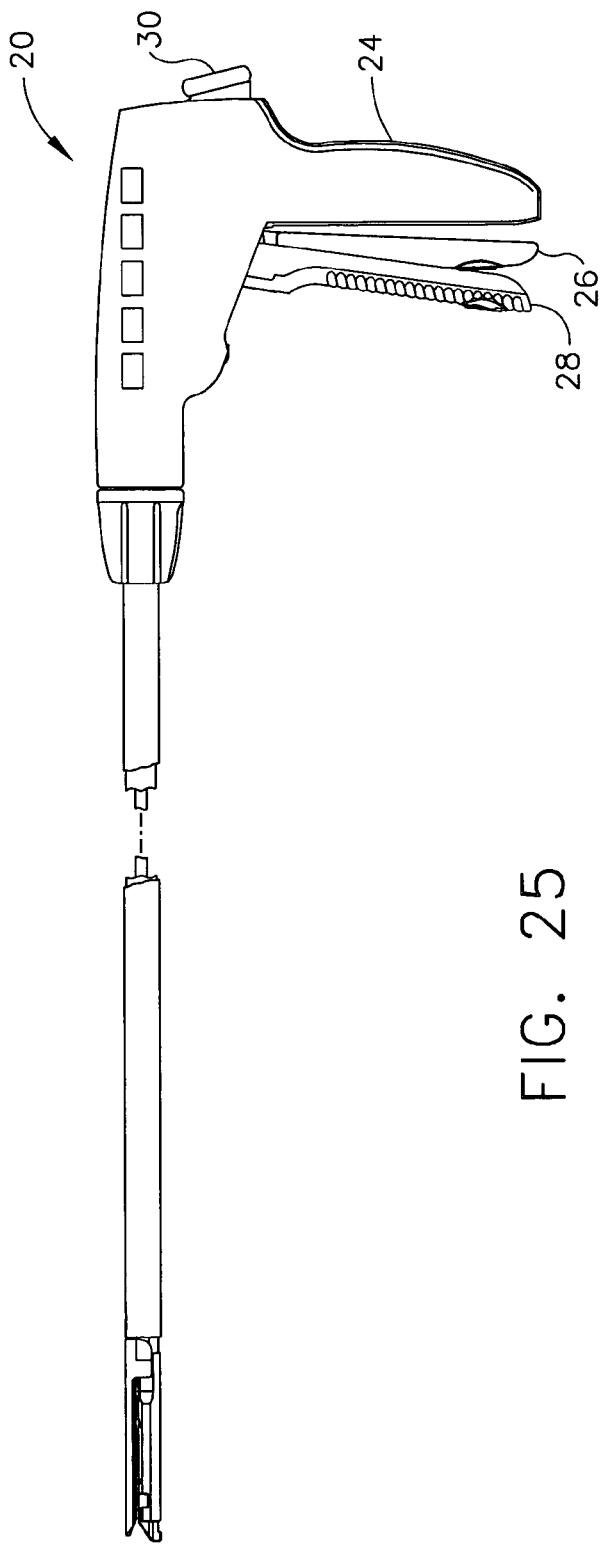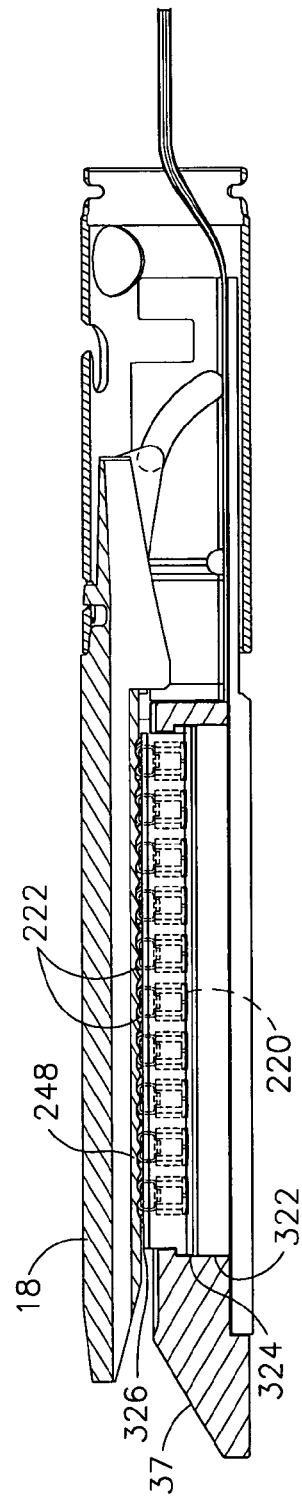

SURGICAL INSTRUMENT HAVING A HYDRAULICALLY ACTUATED END EFFECTOR

FIELD OF THE INVENTION

The present invention relates in general to surgical instruments, and more particularly to endoscopic surgical instruments having a hydraulically actuated end effector.

Endoscopic surgical instruments typically include an end effector positioned at the distal end of an elongate shaft and a handle at the proximal end of the elongate shaft allowing a clinician to manipulate the end effector. In use, the end effector is provided to a surgical site through a cannula of a trocar. At the surgical site, the end effector engages tissue in any number of ways to achieve a diagnostic or therapeutic effect. Endoscopic surgical instruments are often preferred over traditional open surgical instruments because they require smaller incisions that generally heal with less post-operative recovery time than traditional open surgery incisions. Because of this and other benefits of endoscopic surgery, significant development has gone into a range of endoscopic surgical instruments having end effectors that engage tissue to accomplish a number of surgical tasks. For example, end effectors have been developed to act as endocutters, graspers, cutters, staplers, clip appliers, access devices, drug/gene therapy delivery devices, ultrasound, RF, or laser energy devices, and other surgical instruments.

Endoscopic surgical instruments must be configured to generate motion at the end effector in response to input from the handle or other input device, which is separated from the end effector by the narrow elongate shaft. This creates a considerable design challenge as the motions necessary at the end effector can be quite complex and may include motions transverse to the axis of the elongate shaft. One existing design includes a drive band extending from the instrument's handle to the end effector, through or around the elongate shaft. In response to inputs from the handle, the drive band is translated axially toward the end effector. End effector motions along the axis of the elongate shaft are derived directly from the drive band. Non-axial end effector motions, however, such as transverse stapling and clamping motions, must be derived by re-directing the axial drive motion. Often this is accomplished with reciprocating wedges or other mechanical devices. An example of this design is disclosed in U.S. Application Publication No. 2004/0232196 A1, the disclosure of which is herein incorporated by reference in its entirety.

Surgical instruments utilizing the axial drive band design described above present a number of disadvantages. For example, friction between the axial drive band and the shaft generates significant energy loss. This energy loss is exacerbated in instruments having an articulating end effector as the axial drive band must then be translated through an articulation pivot. Mechanical re-directing devices cause additional energy losses because of their inefficiency. Mechanical re-directing devices are also bulky, adding to the overall diameter of the end effector and limiting its use in small surgical environments. Axial drive band devices also provide limited options for operating the end effector. For example, in a stapling instrument having staples driven by a reciprocating wedge, there is no way to fire the more distally located staples without firing the staples between, as the wedge sled must be translated through the positions of the proximally located staples first. It can then be appreciated that staple firing patterns available to reciprocal wedge staplers are quite limited.

It is known to replace the axial drive band described above with axially directed hydraulic cylinders in the end effector. The cylinders provide axial motion to components within the end effector. Non-axial motions are still obtained by re-directing the axial motion provided by the cylinders with reciprocating wedge sleds or other mechanisms. Although this design eliminates the axial drive band and the associated frictional losses, it does not address other problems associated with mechanical re-directing devices such as, added bulk to the end effector, the inefficiencies of mechanical re-direction, and limited firing patterns.

Accordingly there is a significant need for improved surgical instruments with smaller end effectors that are capable of use in smaller surgical sites. There is also a significant need for improved surgical instruments that can translate firing force to an end effector with increased efficiency. In addition, there is a significant need for improved surgical staplers that have a greater range of firing pattern options.

BRIEF SUMMARY OF THE INVENTION

In accordance with one embodiment of the invention, there is provided a hydraulically actuated surgical instrument. The instrument may comprise a handle portion and a shaft mechanically coupled to the handle. The instrument may also include an end effector mechanically coupled to the shaft along its longitudinal axis. The end effector may comprise a surgical implement and a hydraulic device. At least a portion of the surgical implement may be translatable along a transverse axis, wherein the transverse axis is substantially perpendicular to the longitudinal axis of the shaft. Also, the hydraulic device may be positioned to be expandable toward the surgical instrument in a direction substantially parallel to the transverse axis of the shaft.

In accordance with another embodiment of the invention, there is provided an end effector for use with a surgical fastening instrument. The end effector may be configured to drive surgical fasteners in a first direction, and may comprise a surgical fastener cartridge comprising a surgical fastener oriented in the first direction. The end effector may also comprise a fastener hydraulic device positioned to be expandable in the first direction toward the surgical fastener.

In accordance with yet another embodiment of the invention, there is provided a surgical instrument comprising a valve unit, a first surgical implement, and a first hydraulic device. The first hydraulic device may be fluidically coupled to the valve unit and positioned to be expandable toward the first surgical implement. The surgical instrument may also comprise a second surgical implement and a second hydraulic device. The second hydraulic device may be fluidically coupled to the valve unit and positioned to be expandable toward the second surgical implement. The surgical instrument may also comprise a firing pattern control device in communication with the valve unit. The firing pattern control device may configure the valve unit to direct pressurized hydraulic fluid to the first and second hydraulic devices according to a firing pattern.

BRIEF DESCRIPTION OF THE FIGURES

The accompanying drawings, which are incorporated in and constitute part of the specification, illustrate embodiments of the invention and, together with the general description of the invention given above, and the detailed description of the embodiments given below, serve to explain the principles of the present invention.

FIG. 1 depicts a partially cut-away side elevation view of a surgical instrument in an open position according to various embodiments of the present invention;

FIG. 2 depicts a cross-sectional side elevation detail view along the line 2-2 of FIG. 1 of an end effector of the surgical instrument in an up or open position according to various embodiments of the present invention;

FIG. 10 depicts a three dimensional, exploded view of the implement portion of the surgical stapling and severing instrument of FIG. 1 according to various embodiments of the present invention;

FIG. 25 depicts a partially cut-away side elevation view of the surgical stapling and severing instrument of FIG. 1 in a fully fired position according to various embodiments of the present invention; and FIG. 26 depicts a side elevation view in centerline section of the distal end of the surgical stapling and severing instrument of FIG. 1 in a fully fired position according to various embodiments of the present invention.

DETAILED DESCRIPTION OF THE INVENTION

Figure 3:
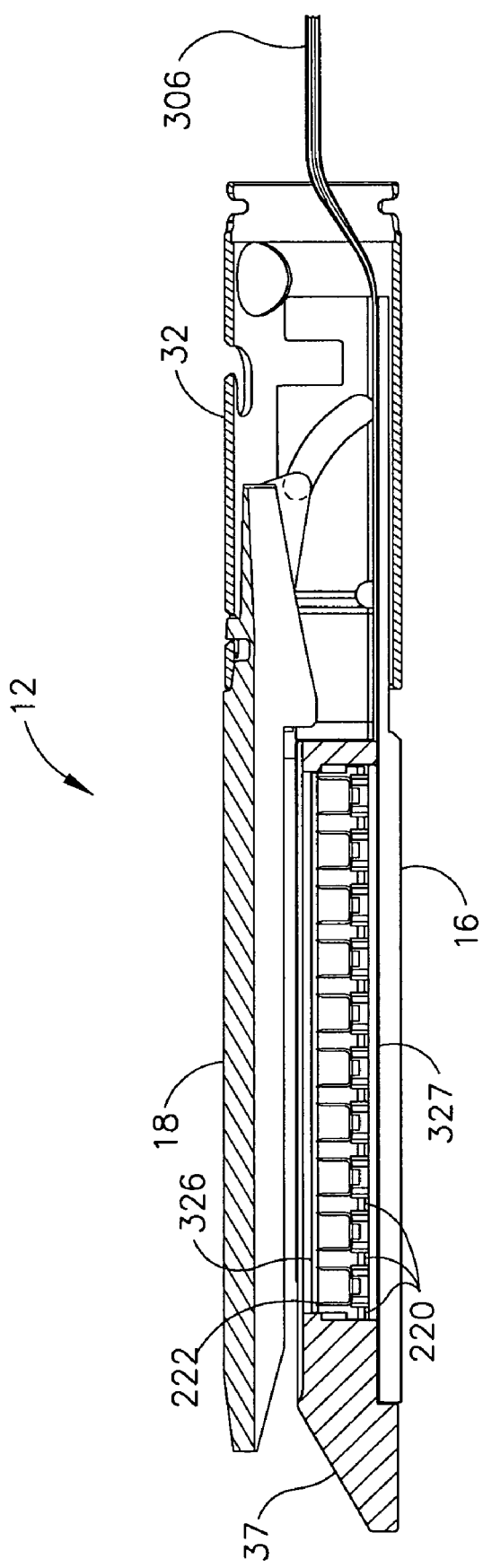
FIG. 3 depicts a cross-sectional side elevation detail view along the line 2-2 of FIG. 1 of an end effector of the surgical instrument in a down or closed position according to various embodiments of the present invention.

The terms "proximal" and "distal" are used herein with reference to a clinician gripping a handle of an instrument. For example, referring to the surgical instrument 10 shown in FIG. 1, the end effector 12 is distal with respect to the more proximal handle portion 20. It will be further appreciated that for convenience and clarity, spatial terms such as "vertical" and "horizontal" are used herein with respect to the drawings. However, surgical instruments are used in many orientations and positions, and these terms are not intended to be limiting and absolute.

As used herein, the term "surgical implement" refers to a component or set of components configured to engage tissue to accomplish a surgical task. Examples of surgical implements include, but are not limited to: endocutters, graspers, clamps, cutters, staplers, other surgical fasteners, clip appliers, probes or access devices, drug/gene therapy delivery devices, energy devices such as ultrasound, RF, or laser devices, etc.

As used herein, the term "surgical fastener" refers to any kind of fastener used in surgical settings including, for example, a staple, a hernia tacker, etc. As used herein, the term "surgical fastener" may also refer to a device for deploying a staple, hernia tacker, etc.

As used herein, the term "fluidically coupled" means that the elements are coupled together with an appropriate line or other means to permit the passage of pressurized fluid medium, air, etc. therebetween. As used herein, the term "line" as used in "supply line," "hydraulic line" or "return line" refers to an appropriate fluid passage formed from conduit, pipe, tubing, etc. for transporting pressurized hydraulic fluid from one component to another.

As used herein, the term, "hydraulic fluid" refers to any fluid suitable for use in a hydraulic system. Non-limiting examples of hydraulic fluids include oil, air, etc. In one non-limiting embodiment, hydraulic fluids may be biocompatible fluids including, for example, glycerine oil, saline, etc.

Turning to the figures, the surgical instrument 10 of FIG. 1 includes a handle portion 20 and an implement portion 22. The implement portion 22 includes a shaft 23 and an end effector 12. The end effector 12 shown in FIG. 1 is configured to act as an endocutter including surgical implements for clamping, stapling and severing, however, it will be appreciated that the advantages of the present invention may be achieved with end effectors (not shown) including alternate and/or additional surgical implements.

Referring back to the non-limiting embodiment shown in FIG. 1, the handle portion 20 of the instrument 10 includes a pistol grip 24 toward which a closure trigger 26 is pivotally drawn by a clinician to cause clamping, or closing, of the anvil 18 toward the elongate channel 16 of the end effector 12. A firing trigger 28 is farther outboard of the closure trigger 26 and is pivotally drawn by the clinician to cause the stapling and severing of clamped tissue in the end effector 12.

The force necessary to cause the closure, stapling, and severing of tissue may be provided by a plurality of hydraulic devices (not shown in FIG. 1) located in the end effector 12 such as, for example, bladders, cylinders, etc. In various embodiments, the hydraulic devices may be supplied with pressurized hydraulic fluid via hydraulic line bundle 306 extending from handle 20 of the instrument 10 to the end effector 12, for example, through the elongate shaft 23.

FIGS. 2-5 show views of the end effector 12 configured to perform clamping, severing and stapling of tissue according to various embodiments the present invention. The end effector 12 may include anvil 18 and elongate channel 16 configured to receive a staple cartridge 37. The anvil 18 may pivot towards the elongate channel 16 and staple cartridge 37 about anvil pivot 14. FIG. 2 shows the anvil 18 in an open position, while FIG. 3 shows the anvil 18 in a pivoted or closed position.

Force necessary to pivot or drive the anvil 18, in various embodiments, may be provided by closure sleeve 32. For example, when the clinician actuates closure trigger 26, the closure sleeve 32 may be translated distally toward the end effector driving the anvil 18 into the closed position shown in FIG. 3. When the closure trigger 26 is released, the closure sleeve 32 may be translated proximally away from the end effector 12. The instrument 10 may include a spring or other energy storage device causing the anvil 18 to return to the open position shown in FIG. 2 when the closure sleeve 32 is retracted. Force may be transferred from the closure trigger 26 to the closure sleeve 32 by any mechanism known in the art including, for example, a gear system, an electric motor, a hydraulic device, etc.

Referring back to FIG. 2, the end effector 12 may include a transversely presented cutting edge 326. The cutting edge 326 may be driven by a hydraulic cutting bladder 322 positioned below the cutting edge 326. A cutting bar 324 may be positioned between the cutting bladder 322 and cutting edge 326. In various embodiments, the cutting bladder 322, bar 324 and edge 326 may be fastened to one another. It will be appreciated that the hydraulic cutting bladder 322, in various non-limiting embodiments, may be replaced by any kind of hydraulic device including, for example, a hydraulic cylinder. In response to a clinician actuating the firing trigger 28, the hydraulic cutting bladder 322 may expand in a transverse direction. This drives the cutting edge 326, causing it to move through the elongate channel 16 and staple cartridge 37 in a transverse direction and sever any tissue (not shown) present between the anvil 18, staple cartridge 37 and elongate channel 16, for example, as described in more detail below with reference to FIGS. 20-26.

Referring again to FIG. 3 a cross sectional view of the end effector 12 is shown including staples 222 and staple drivers 220 according to various embodiments. A plurality of staples 222 and staple drivers 220 are shown positioned adjacent the cutting edge 326. Each staple driver 220 may be positioned below one, or a plurality of staples 222 included in the staple cartridge 37. A staple hydraulic bladder 327 may be positioned below the staple drivers 220. The staple hydraulic bladder 327 may be expandable in a transverse direction toward staple drivers 220. The staple hydraulic bladder 327 may expand in response to the actuation of the firing trigger 28 by the clinician. Expansion of the staple hydraulic bladder 327 forces the staple drivers 220 and staples 222 toward staple forming pockets (not shown in FIG. 3) present in the anvil 18, thus driving the staples.

Figure 4:
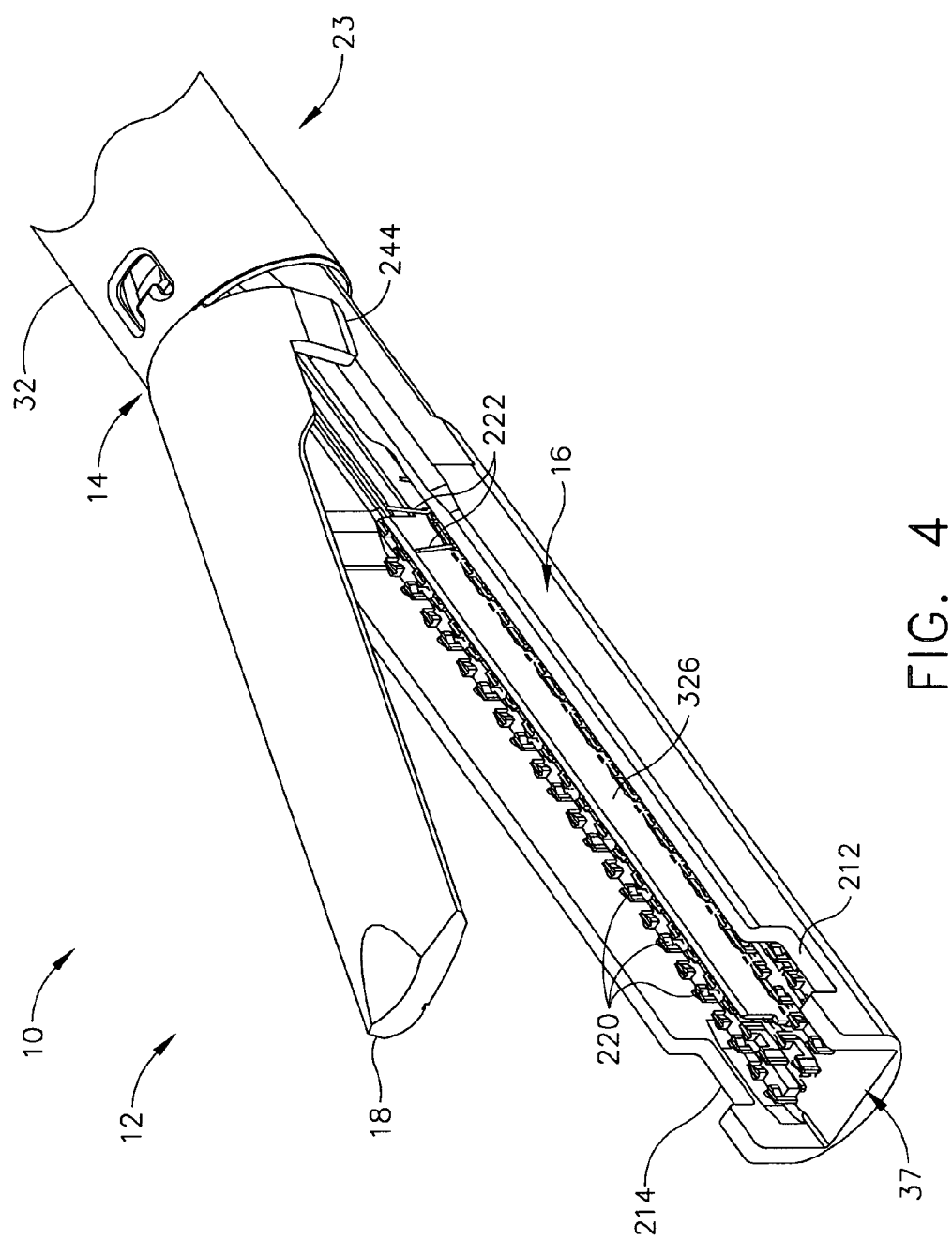
FIG. 4 depicts a three dimensional view of the end effector at the distal end of the surgical stapling and severing instrument of FIG. 1 with the anvil in the up or open position and portions of the cartridge largely removed exposing exemplary staple drivers and an exemplary cutting edge according to various embodiments of the present invention.

FIG. 4 shows a three dimensional view of the end effector 12 of the instrument 10 with a portion of the staple cartridge 37 removed to expose features of the elongate channel 16, such as recesses 212, 214, and components of the staple cartridge 37, such as staple drivers 220, in their unfired position. The cutting edge 326 is shown at its unfired position, located in the center of staple drivers 220. FIG. 4 also shows tissue stops 244 located at the proximal end of the anvil 18. Tissue stops 244 may, in various embodiments, prevent tissue from coming into contact with components of the anvil pivot 14, causing the end effector 12 to jam.

Figure 5:
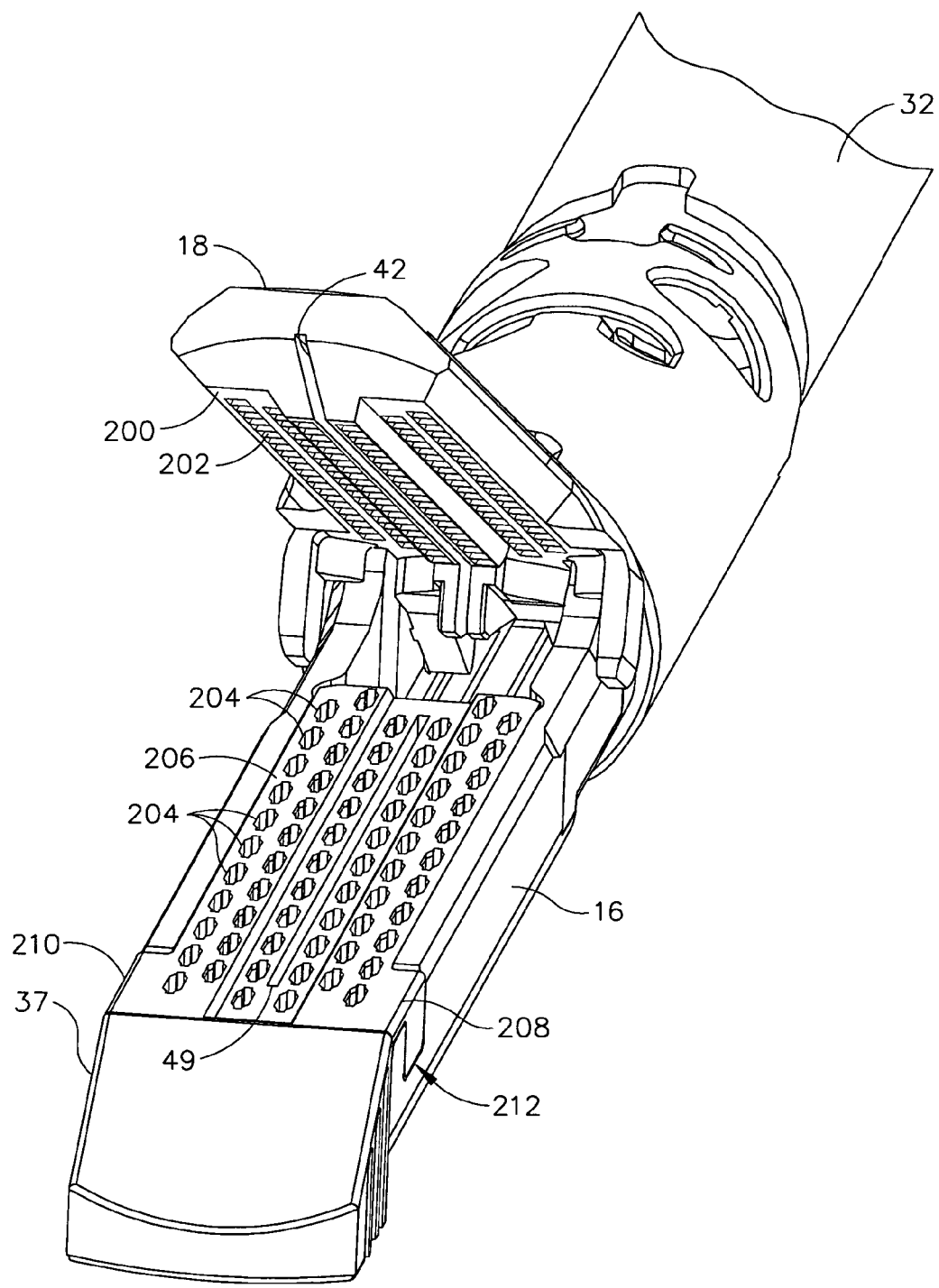
FIG. 5 depicts a three dimensional view of an end effector at the distal end of the surgical stapling and severing instrument of FIG. 1 with the anvil in the up or open position exposing the staple cartridge and cutting according to various embodiments of the present invention.

FIG. 5 depicts a three dimensional view of the end effector 12 in an open position with a staple cartridge 37 installed in the elongate channel 16. On a lower surface 200 of the anvil 18, a plurality of stapling forming pockets 202 are arrayed to correspond to a plurality of staple apertures 204 in an upper surface 206 of the staple cartridge 37. Each aperture 204 may correspond to an individual staple 222 located within the staple cartridge 37 immediately below the aperture 204 as shown in FIG. 3. Slot 49, positioned in the middle of the staple cartridge 37, may enclose the cutting edge 326 (not shown in FIG. 5). The staple cartridge 37 may be snap-fit into the elongate channel 16. For example, extension features 208, 210 of the staple cartridge 37 engage recesses 212, 214 (shown in FIG. 4) of the elongate channel 16.

Figure 6:
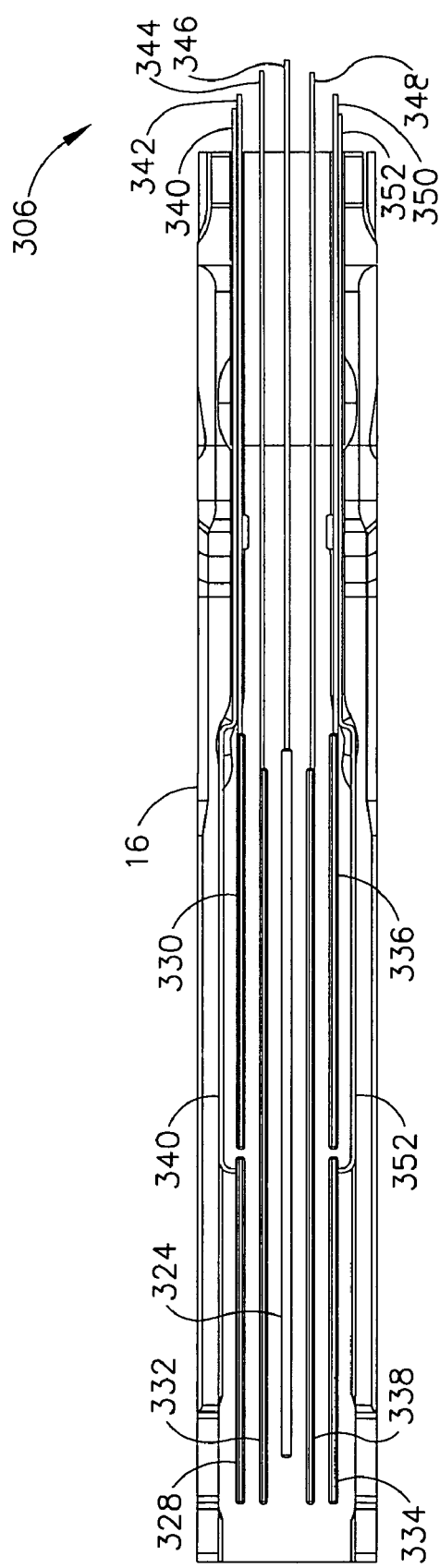
FIG. 6 depicts a two dimensional top-down view of an elongate channel of the surgical stapling and severing instrument of FIG. 1 according to various embodiments of the present invention.
Figure 7:
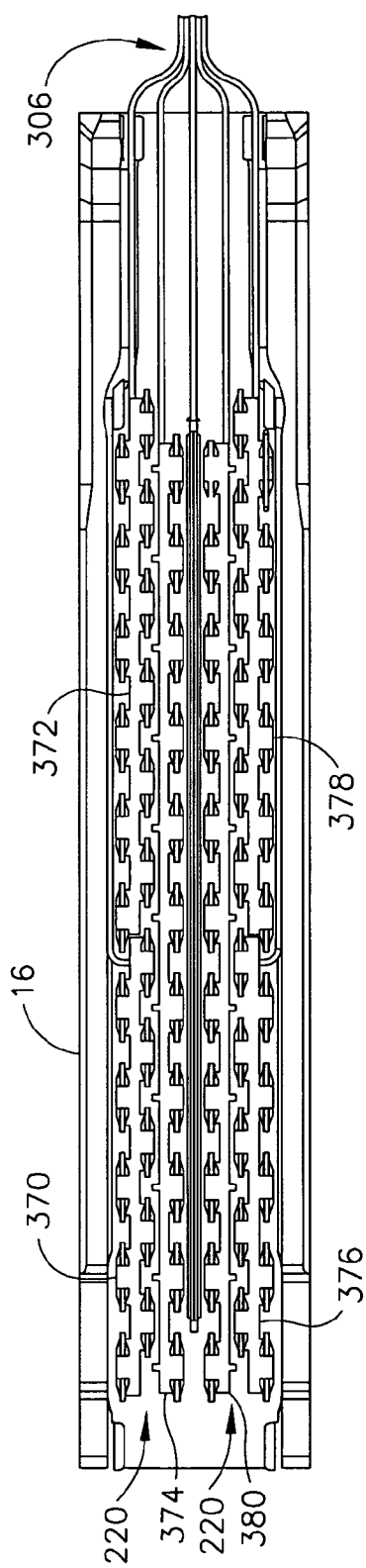
FIG. 7 depicts a two dimensional top-down view of a staple cartridge installed in an elongate channel with a portion of the staple cartridge removed to show exemplary staple drivers according to various embodiments of the present invention.
Figure 8:
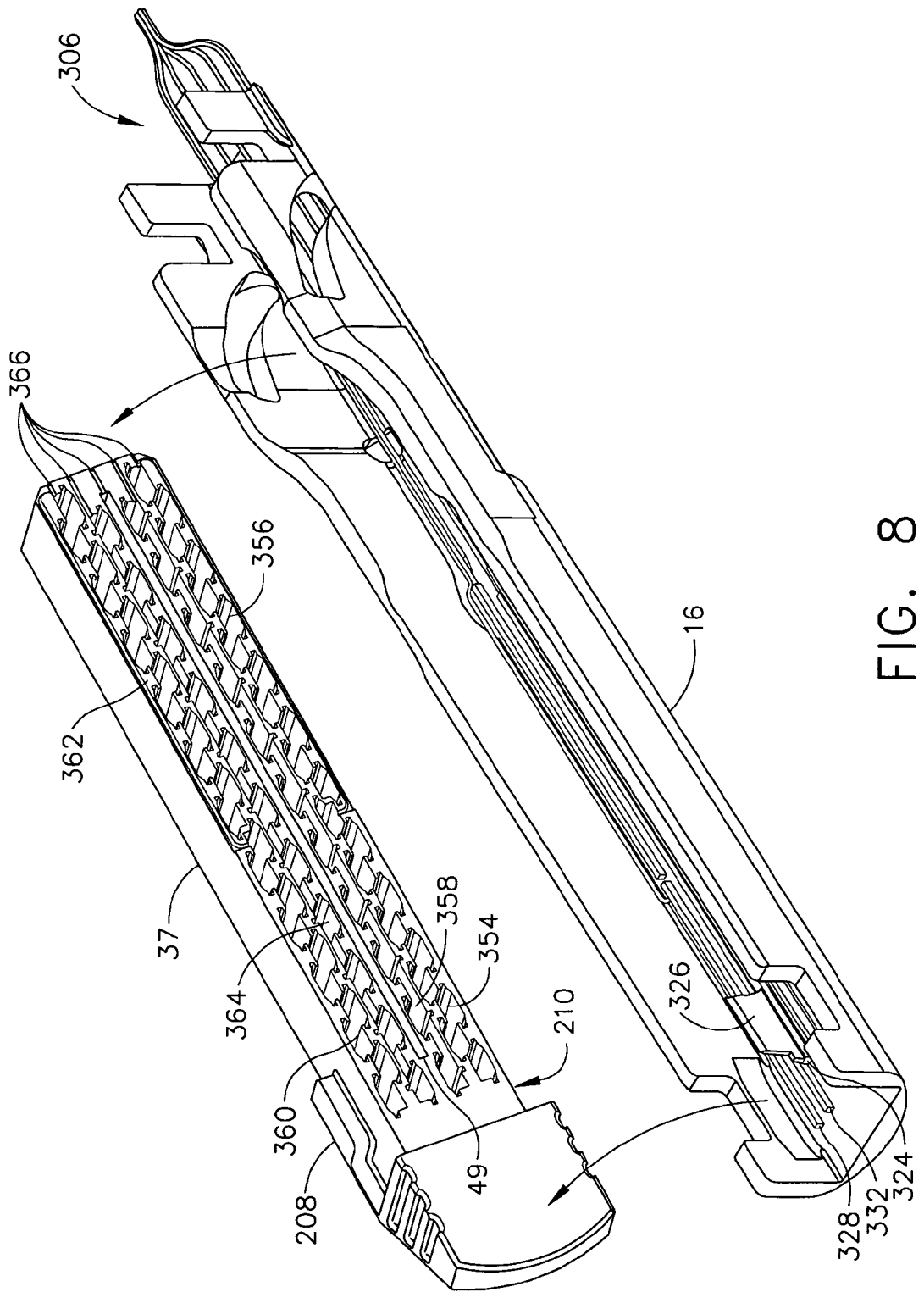
FIG. 8 depicts a three dimensional view of the elongate channel of the surgical stapling instrument of FIG. 1 showing a staple cartridge according to various embodiments of the present invention.

In various embodiments, staples 222 included in the end effector 12 may be driven according to one or more staple zones, with each staple zone able to be fired or driven separately. FIGS. 6-8 show a non-limiting zoned embodiment including six staple zones, with each staple zone including one hydraulic device and one staple driver configured to drive a plurality of staples. For example, a right distal staple zone includes right distal staple bladder 332 (shown in FIG. 6), and right distal staple driver 370 (shown in FIG. 7). It will be appreciated that various non-limiting embodiments of the present invention may include more or fewer than six staple zones depending on the application, with each zone including as many or as few staples as desired. It will also be appreciated that that individual staple zones according to various embodiments of the present invention may include multiple staple bladders and/or staple drivers.

Referring back to FIG. 6, a top down view of the elongate channel 16 is shown including six hydraulic staple bladders 328, 330, 332, 334, 336 and 338. Each of the bladders may correspond to one of the six zones of staples. The bladders 328, 330, 332, 334, 336, 338 as well as cutting bladder 322 (positioned below cutting bar 324 in FIG. 10) may be individually provided with pressurized hydraulic fluid through respective hydraulic lines 340, 342, 344, 346, 348, 350, 352 included in hydraulic line bundle 306. Accordingly, in various embodiments, each of bladders 328, 330, 334, 336, 338 and 322 may drive associated surgical implements individually or according to a firing pattern.

FIG. 7 shows a top down view of the elongate channel 16 and staple cartridge 37 with the upper surface 206 of the staple cartridge 37 removed to show staple drivers 370, 372, 374, 376, 378, 380. Each staple driver may correspond to one of the six staple zones. Also, each staple driver 370, 372, 374, 376, 378, 380 is positioned above the staple bladder 328, 330, 332, 334, 336, 338 (shown in FIG. 10) corresponding to the same staple zone. For example, right distal staple bladder 332 is positioned above the right distal staple driver 370. It will be appreciated that it is not necessary to have only one staple driver corresponding to each staple bladder 328, 330, 332, 334, 336, 338. For example, in one non-limiting embodiment, a staple driver 220 may be provided for each individual staple 222.

FIG. 8 shows an exploded three dimensional view of the elongate channel 16 with staple cartridge 37 implementing the staple zone scheme shown in FIGS. 6 and 7. The staple cartridge 37 may include staple recesses 354, 356, 358, 360, 362, 364. Each staple recess may house staples 222 (not shown in FIG. 8) and one of staple drivers 370, 372, 374, 376, 378 (not shown in FIG. 8). When the staple cartridge 37 is installed in the elongate channel 16, each staple recess, including staples 222 and the staple drivers described above, may align with at least one staple bladder 328, 330, 332, 334, 336, 338. When the staple bladders 328, 330, 332, 334, 336, 338 are inflated, they may extend into the staple recesses 354, 356, 358, 360, 362, 364, creating a transverse force against the staple drivers 370, 372, 374, 376, 378, which in turn drive the staples 222. FIG. 8 also shows that the staple cartridge 37 may include channels 366 for receiving hydraulic lines 340, 342, 344, 346, 348, 350, 352, shown in FIG. 10. The channels 366 prevent the various hydraulic lines from being pinched between the staple cartridge 37 and the elongate channel 16.

Figure 9:
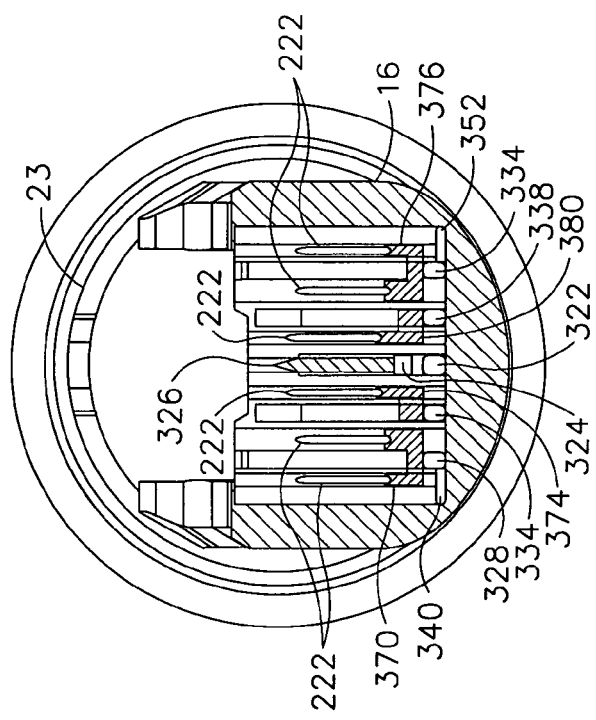
FIG. 9 depicts a section view showing the cross-sectional relationship between the hydraulic bladders according to various embodiments of the present invention.

FIG. 9 shows a cross-sectional view of the end effector 12 showing the configuration of bladders 328, 334, 322, 338 and 334 according to various embodiments. Bladder 328 is shown positioned below staple driver 370. Inflating bladder 328 causes a transverse force to be exerted on the driver 370, which may drive the staple 222. The other staple bladders 334, 338 and 334 shown in FIG. 9 may operate in a similar fashion. Cutting bladder 322 may also create a transverse force when inflated. The transverse force may cause cutting bar 324 to rise transversely, pushing cutting edge 326 transversely through any tissue (not shown) present in the end effector 12.

FIG. 10 shows the implement portion 22 of the surgical stapling and severing instrument 10 in disassembled form. The staple cartridge 37 is shown comprised of a cartridge body 216, staple drivers 370, 372, 374, 376, 378, 380, cutting edge 326 and staples 222. When assembled, the cartridge body 216 holds the staple drivers 370, 372, 374, 376, 378, 380 and staples 222. When the implement portion 22 is assembled, cutting bladder 322, cutting bar 324 and cutting edge 326 may be positioned along the elongate channel 16 as shown. Staple bladders 328, 330, 332, 334, 336, 338 may also be positioned along the elongate channel 16 and may be used to drive staples 222, for example, according to the zoned scheme described above. The staple cartridge 37 may be placed in the elongate channel 16 such that the cutting bladder 322, cutting bar 324 and cutting edge 326 align with channel 49 and such that lines of staples 222 and drivers 370, 372, 374, 376, 378, 380 align with bladders 328, 330, 332, 334, 336, 338.

Figure 11:
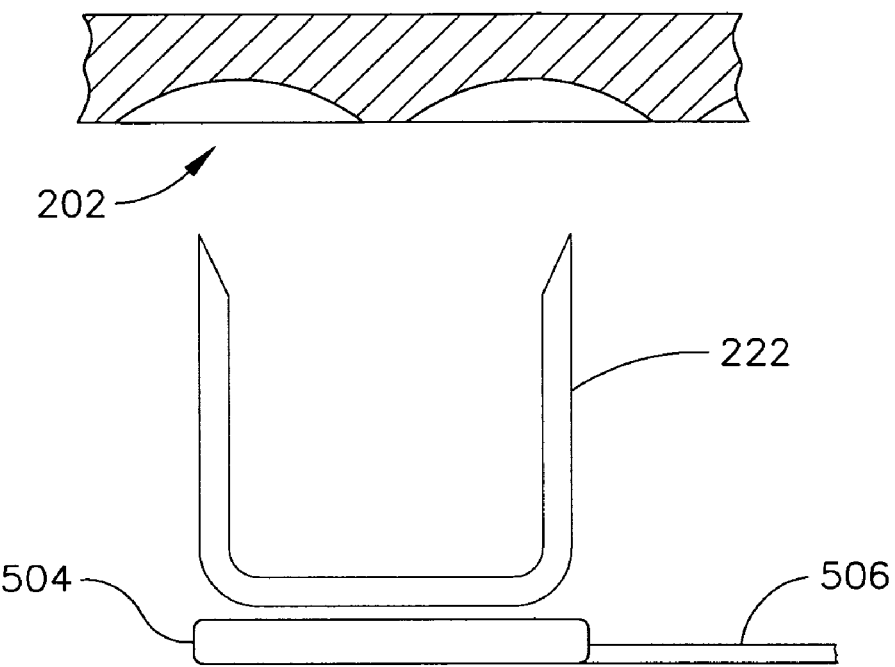
FIG. 11 depicts an un-inflated hydraulic bladder staple driver for use in a surgical instrument according to various embodiments of the present invention.
Figure 12:
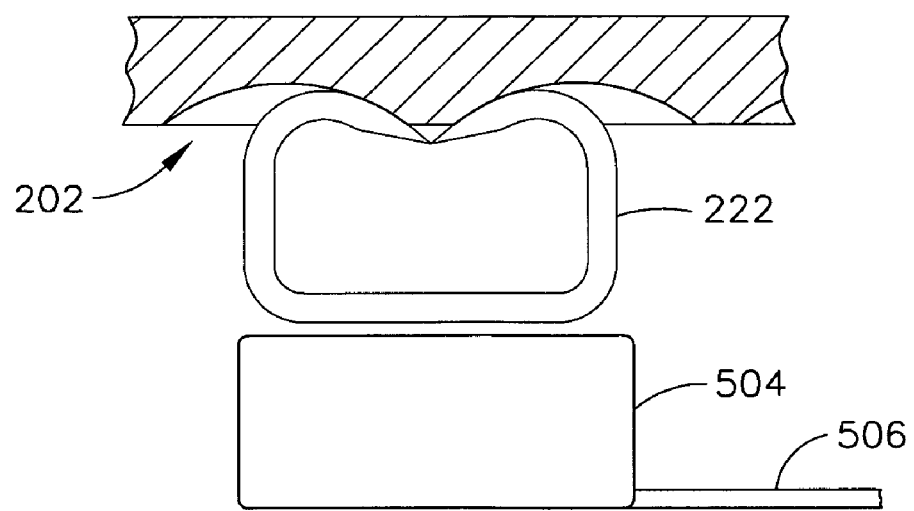
FIG. 12 depicts an inflated hydraulic bladder staple driver for use in a surgical instrument according to various embodiments of the present invention.

The embodiments described above show staples 222 resting on a staple bladder 327, or staple bladders 328, 330, 332, 334, 336, 338, with various staple drivers 220 therebetween. It will be appreciated, however, that in various non-limiting embodiments, staples may be hydraulically driven utilizing other mechanisms. For example, FIGS. 11-12 show a staple 222 resting directly on a staple bladder 504 (e.g., without a staple driver). A hydraulic line 506 may provide pressurized hydraulic fluid to the bladder 504, for example, in response to the actuation of the firing trigger 28 by the clinician. When pressurized hydraulic fluid is provided to the staple bladder it may expand transversely, as shown in FIG. 12. The transverse motion of the staple bladder 504 may force the staple 222 against staple forming pocket 202, thereby driving the staple 222. The assembly shown in FIGS. 11-12 may be incorporated into the end effector 12, for example, by placing a staple bladder or bladders 504 along the elongate channel 16. It will be appreciated that in various embodiments, each bladder 504 may drive one or a plurality of staples 222.

Figure 13:
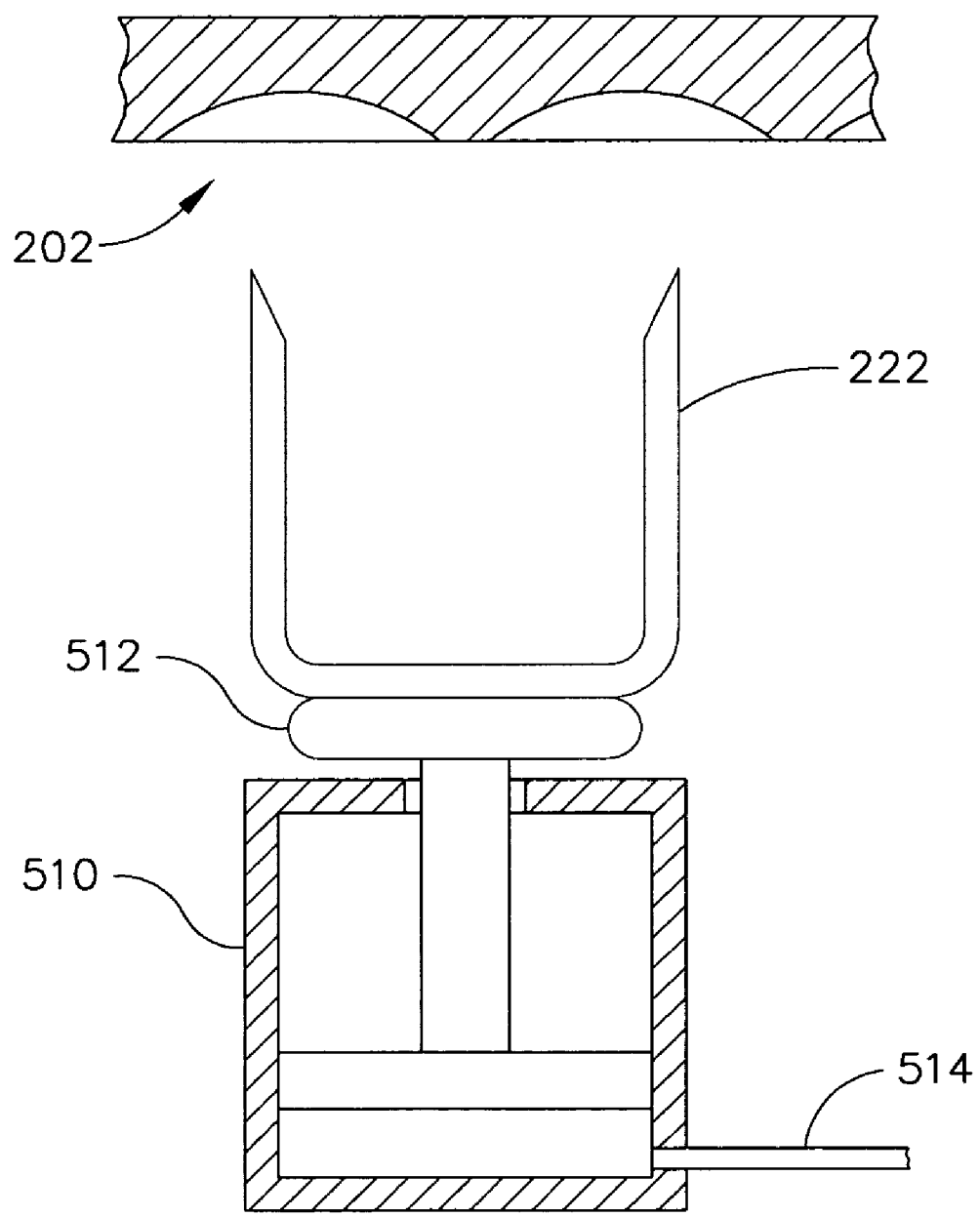
FIG. 13 depicts a hydraulic cylinder staple driver for use in a surgical instrument according to various embodiments of the present invention.

FIG. 13 shows another non-limiting embodiment showing an additional mechanism including a staple driving cylinder 510. The cylinder 510 may include a piston 512. The staple 222 may rest on the piston 512. A staple driver (not shown in FIG. 13) may or may not be present between the piston 512 and the staple 222. A hydraulic line 514 may provide pressurized hydraulic fluid, causing the piston 512 to extend. In response, the piston 512 may drive staple 222 into contact with staple pocket 202 as described above. In various embodiments, the cylinder 510 may drive one or a plurality of staples 222. It will be appreciated that the assembly shown in FIG. 13 may be incorporated into end effector 12 by placing one or more cylinders 510 along the elongate channel 16.

Figure 14:
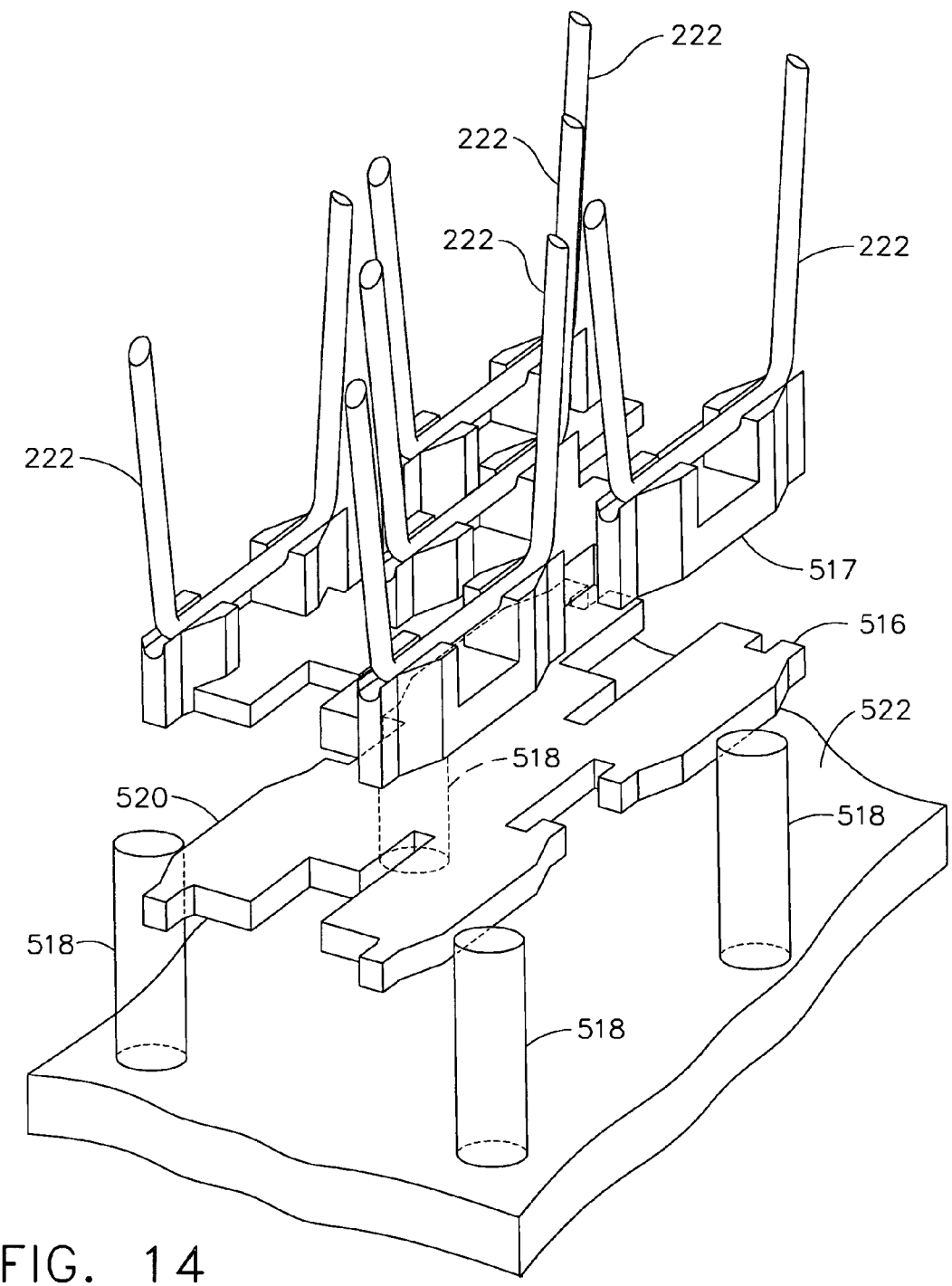
FIG. 14 depicts a hydraulic staple driving assembly for use in a surgical instrument according to various embodiments of the present invention.

FIG. 14 shows an exploded view of another non-limiting exemplary embodiment for hydraulically driving staples according to various embodiments of the present invention. Staples 222 are shown resting on staple driver 517 which in turn rests on deployment plate 516. Guidance rails 518 are shown surrounding the deployment plate 516. When provided with pressurized hydraulic fluid, bladder 522 may expand transversely. This may cause the deployment plate 516 to expand transversely along guidance rails 518, driving staples 222. The guidance rails 518 may insure that deployment plate 516 expands in a transverse direction. In one non-limiting embodiment, staples 222 may rest directly on the deployment plate 516 (e.g., without drivers 517). It will be appreciated that the assembly shown in FIG. 14 may be incorporated into the end effector 12 by placing one or more bladders 522, guidance rails 518, and deployment plates 516 along the elongate channel 16.

Figure 15:
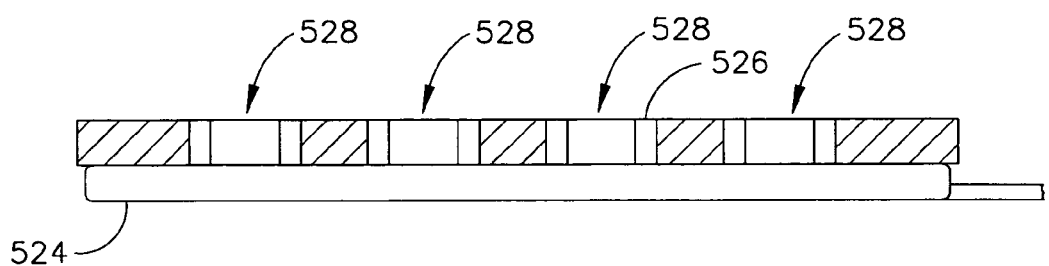
FIG. 15 depicts a side view of a hydraulic staple driving assembly for use in a surgical instrument according to various embodiments of the present invention.
Figure 16:
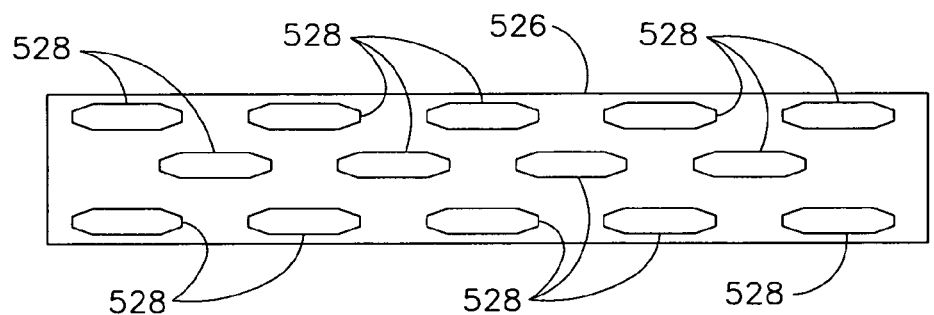
FIG. 16 depicts a top view of a hydraulic staple driving assembly for use in a surgical instrument according to various embodiments of the present invention.
Figure 17:
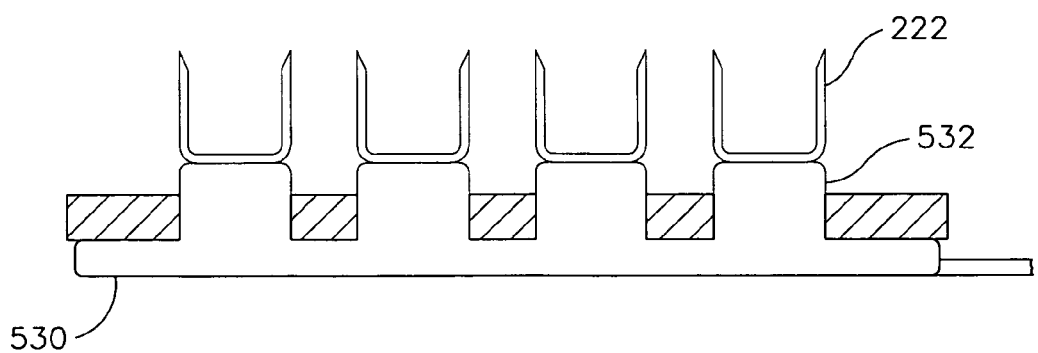
FIG. 17 depicts a side view of a hydraulic staple driving assembly for use in a surgical instrument according to various embodiments of the present invention.

FIGS. 15-17 show yet another non-limiting exemplary embodiment for hydraulically driving staples according to various embodiments. FIG. 15 shows a hydraulic bladder 524 mated to a rigid deployment plate 526. The deployment plate 526 may include a series of apertures 528. Each aperture may correspond to one or more staples. When pressurized hydraulic fluid is applied to the bladder 524, it may expand transversely through the apertures 528 in the deployment plate 526. The portions of the bladder 524 extending through apertures 528 may provide a transverse driving force to one or more staples 222, as shown in FIG. 17.

Figure 18:
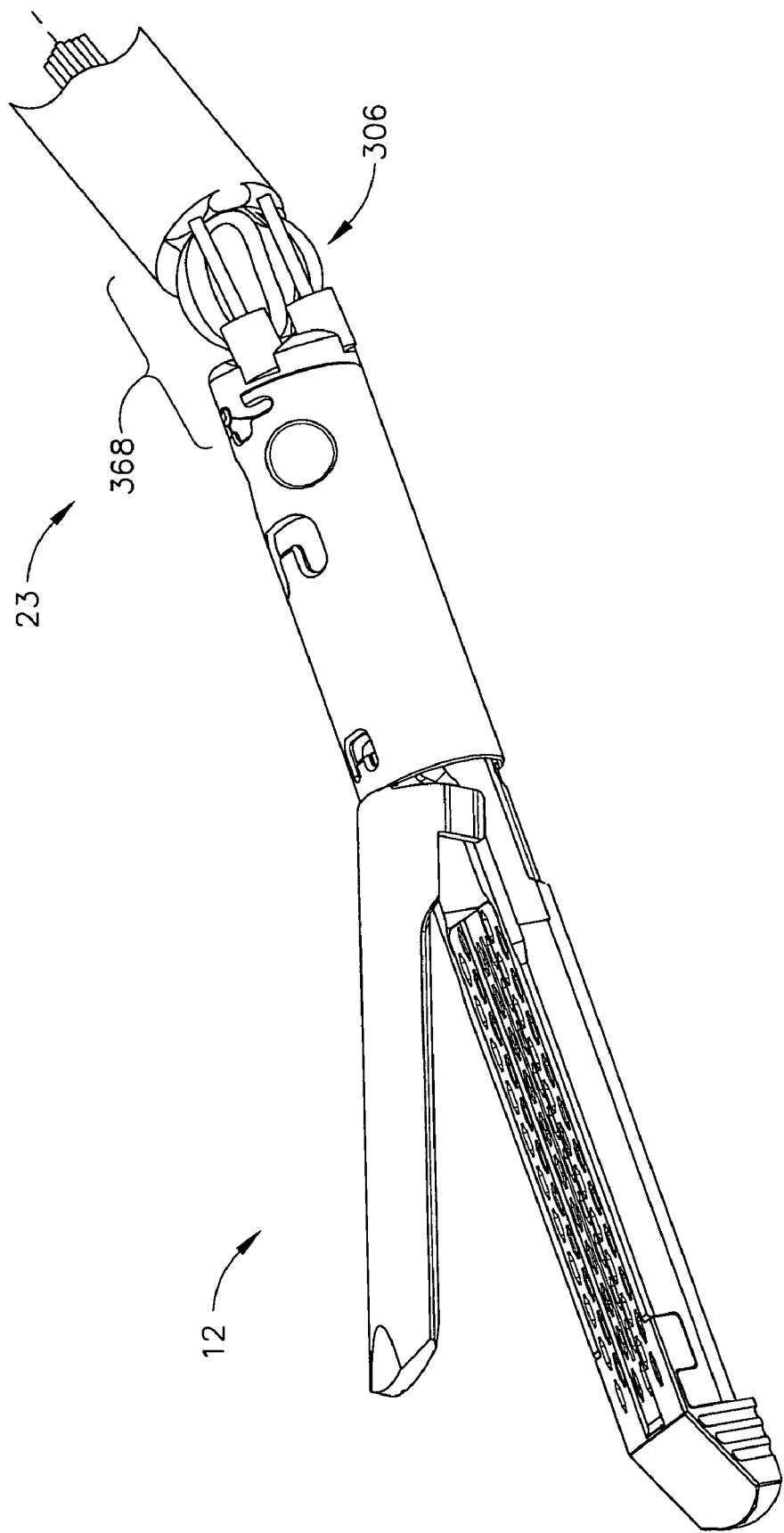
FIG. 18 depicts the distal end of a surgical stapling and severing instrument having an articulating end effector shown in the down or closed position according to various embodiments of the present invention.

In various embodiments, the instrument 10 may include an articulating end effector 12 as shown in FIG. 18. The end effector 12 may pivot away from the axis of the elongate shaft 23 at articulation pivot 368. It can be seen that the hydraulic line bundle 306 passes through articulation pivot 368 with ease.

Figure 19:
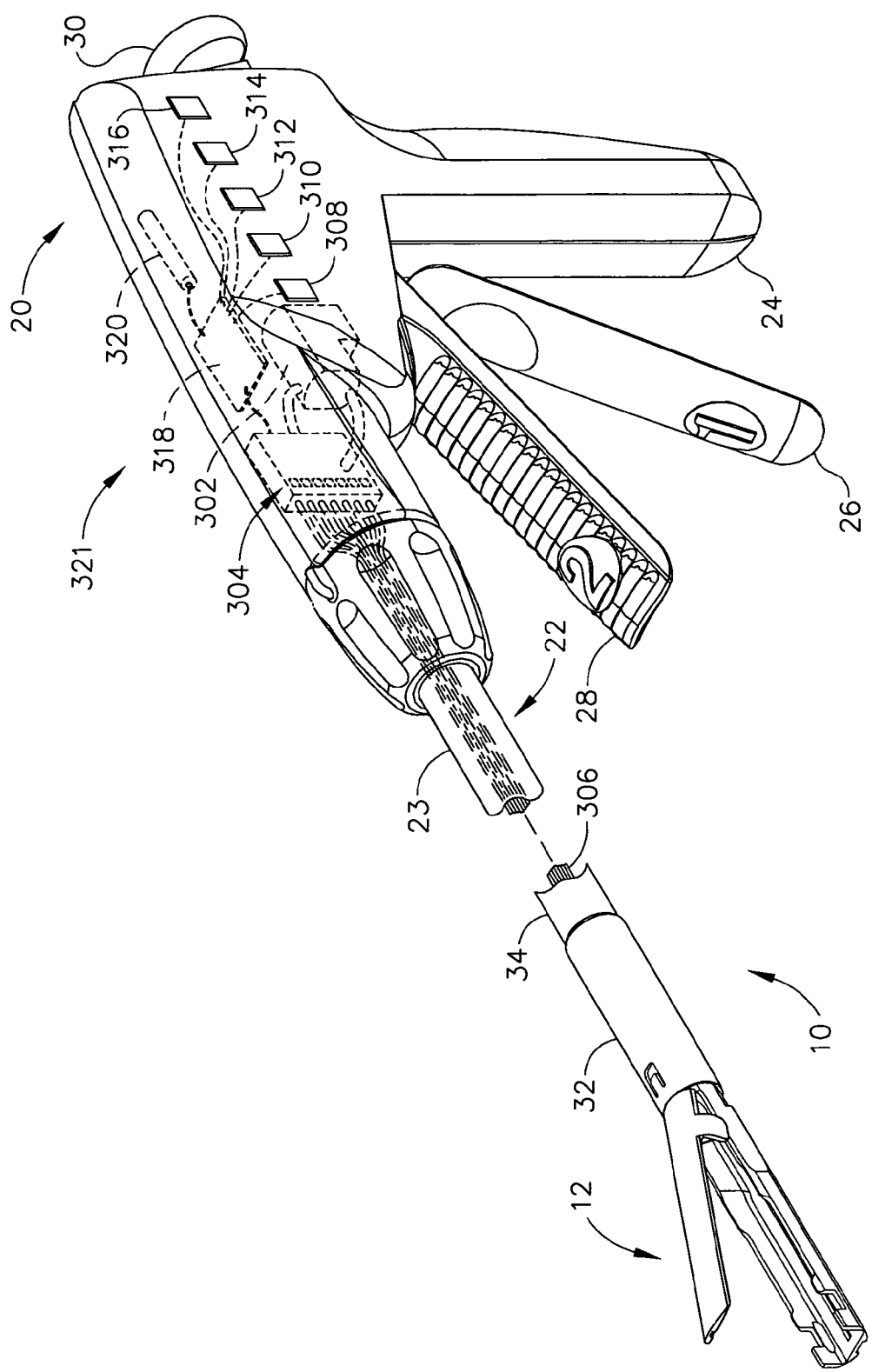
FIG. 19 depicts a three dimensional view of a hydraulic surgical instrument according to various embodiments of the present invention.

FIG. 19 shows an embodiment of the instrument 10 equipped with a hydraulic system 321 according to various embodiments. A hydraulic pump 302 may generate pressurized hydraulic fluid when firing trigger 28 and/or the closure trigger 26 is actuated. The hydraulic pump 302 may be any kind of device suitable for pressurizing hydraulic fluid including, for example, a cylinder, a bladder, etc. In various embodiments, an additional pump (not shown) may be included, for example, to drive the anvil 18 in response to actuation of the closure trigger 26. Pressurized hydraulic fluid generated by the hydraulic pump 302 may be provided to valve unit 304 which may in turn provide the fluid to various bladders and/or cylinders (not shown in FIG. 19) located in the end effector 12 via hydraulic line bundle 306. Valve unit 304 may include any kind of valve or valves suitable for controlling and directing the flow of hydraulic fluid. In various non-limiting embodiments, the valve unit may include electrically actuated valves, such as, for example, piezo valves or Electro Active Polymer (EAP) valves which may be configured in response to an electrical signal.

Figure 19A:
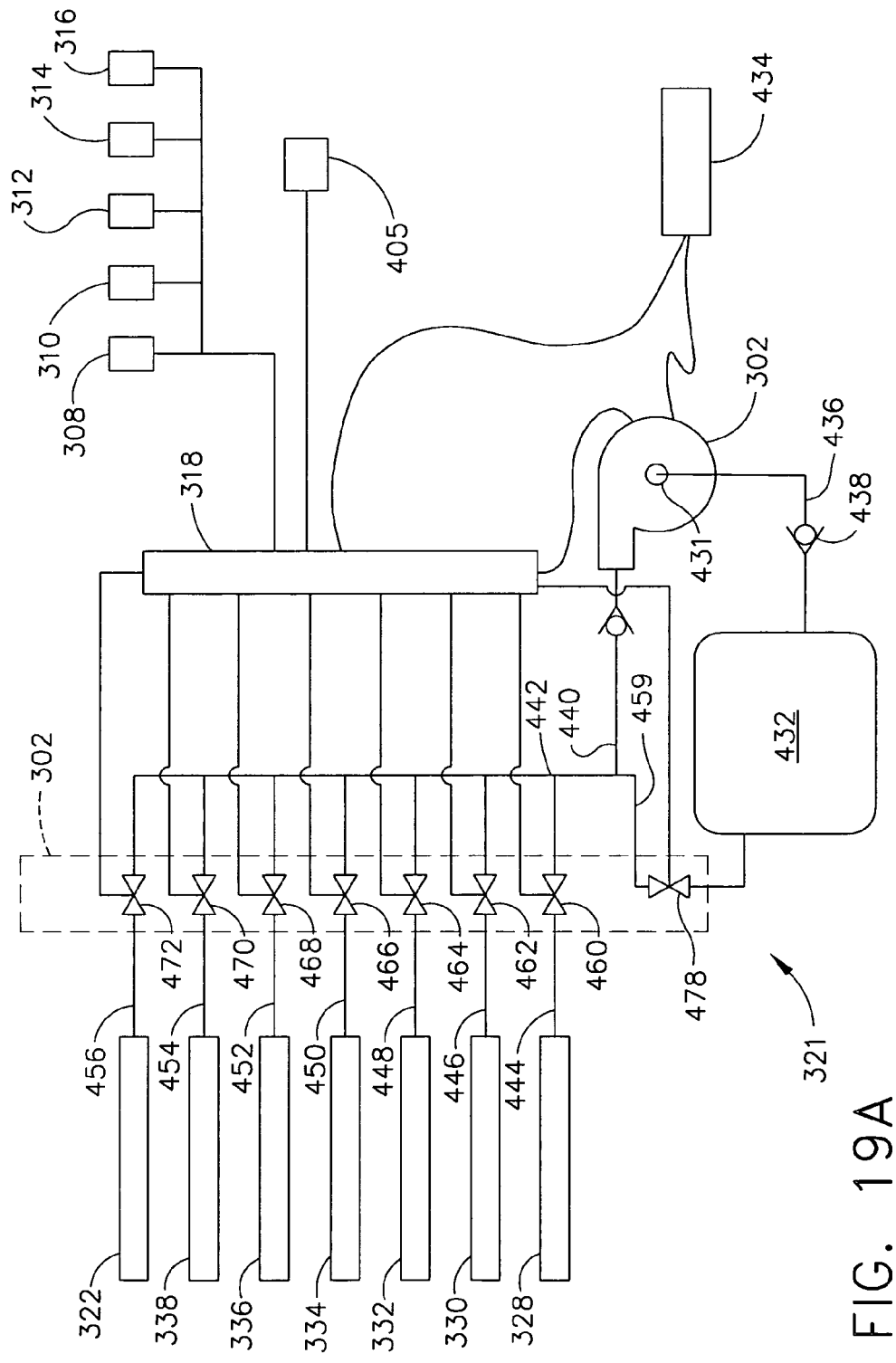
FIG. 19A depicts a schematic diagram of a hydraulic system for use in a surgical instrument according to various embodiments of the present invention.

One embodiment of the hydraulic system 321 that may be employed to control the end effector 12 is depicted in schematic form in FIG. 19A. In this non-limiting embodiment, the pump 302 is embodied as a conventional hydraulic pump assembly that includes a fluid reservoir 432. In one embodiment, the pump 302 is powered by a battery 434 supported within the handle. In another non-limiting embodiment, the pump 302 may be powered by the same battery 320 powering the control circuit 318 described below. It will be appreciated that the pump 302 could also be powered by other means, such as by alternating current. In one non-limiting embodiment, the pump 302 may be a hydraulic bladder or cylinder powered by mechanical force derived from one or more of the triggers 26, 28. The pump 302 may be fluidically coupled to the reservoir 432 by supply line 436 that may have a conventional check valve 438 therein. See FIG. 19A.

In one embodiment, a discharge line 440 attached to the discharge port 431 of the pump 302 is piped to a manifold 442 that has designated supply lines for each bladder coupled thereto. For example, in the embodiment depicted in FIG. 19A, a supply line 444 is coupled to bladder 328 and has a control valve 460 therein for controlling the flow of pressurized fluid through the line 444 to bladder 328. Supply line 446 is coupled to bladder 330 and has a control valve 462 therein. Supply line 448 is coupled to bladder 332 and has a control valve 464 therein. Supply line 450 is coupled to bladder 334 and has a control valve 466 therein. Supply line 452 is coupled to bladder 336 and has a control valve 468 therein. Supply line 454 is coupled to bladder 338 and has a control valve 470 therein. Supply line 456 is coupled to cutting bladder 322 and has control valve 472 therein. A return valve 478 is provided to permit the fluid to return from the bladders into the manifold line 442 and through a return line 459 that is attached to the manifold 442 and the reservoir 432. As can be seen in FIG. 19A, the return line 459 may have a return valve 478 therein. Valves 460, 462, 464, 466, 468, 470, 472, 474, 478 comprise a valve unit, generally designated as 304 and described above.

The valve unit 304 may be configured by a control circuit 318 in response to input received from input buttons, such as buttons 308, 310, 312, 314, and/or 316. A battery 320 may provide electrical power to the control circuit 318 and buttons 308, 310, 312, 314, 316. The control circuit 318 may be any kind of circuit capable of generating signals for configuring valve unit 304 in response to input from buttons 308, 310, 312, 314, 316. In one non-limiting embodiment, the control circuit 318 may include a microprocessor and other related components including Random Access Memory (RAM), Read Only Memory (ROM), etc. In other non-limiting embodiments, the control circuit 318 may include various logical circuit elements.

The control circuit 318 may configure the valves in response to input buttons 308, 310, 312, 314, 316. In one non-limiting embodiment, each input button 308, 310, 312, 314, 316 may correspond to a particular surgical implement, or portion of a surgical implement, included in the end effector 12. For example, button 308 may correspond to a cutter while buttons 310, 312, 314, 316 may each correspond to a zone of staples (not shown in FIG. 2). Selecting the button 308, 310, 312, 314, 316 corresponding to a surgical implement may cause the control circuit 318 to configure the valve unit 304 such that a hydraulic device corresponding to the function is fired when firing trigger 28 is depressed, driving the corresponding surgical implements. Multiple buttons may be selected to create firing patterns including more than one implement. In other non-limiting embodiments, each input button 308, 310, 312, 314, 316 may represent a pre-determined firing order and/or pattern. For example, selecting a button 308, 310, 312, 314, 316 may cause the control circuit 318 to configure the valve unit 304 such that hydraulic devices corresponding to particular surgical implements are fired when the firing trigger 28 is depressed. It will be appreciated that various embodiments may have more or fewer input buttons than are shown.

In various non-limiting embodiments, control circuit 318 may configure the valve unit 304 to introduce a delay to the driving of one or more surgical implements included in the end effector 12. For example, it may be desirable to drive a cutting implement and then delay for a predetermined time before driving one or more zones of a stapling implement. The delay may be accomplished according to any suitable method. In one non-limiting embodiment, the control circuit 318 may configure the valve unit 304 to open a path for hydraulic fluid between the hydraulic pump 302 and a first surgical implement included in the end effector 12. When the firing trigger 28 is actuated, the pump 302 may generate pressurized hydraulic fluid, which drives the first surgical implement. The control circuit 318 may sense when the first surgical implement is driven (e.g., by sensing the position of the firing trigger 28), for example using sensor 405 shown in FIG. 19A. When the first surgical implement is driven, the control circuit 318 may begin a timer that counts off a predetermined delay time. At the expiration of the predetermined delay time, the control circuit 318 may configure the valve unit 304 to provide the pressurized hydraulic fluid to a second surgical implement. Hydraulic pressure generated at the actuation of the firing trigger 28 may be sufficient to drive the second surgical implement, or in various embodiments, the hydraulic pump 302 may be utilized to generate additional hydraulic pressure.

Figure 20:
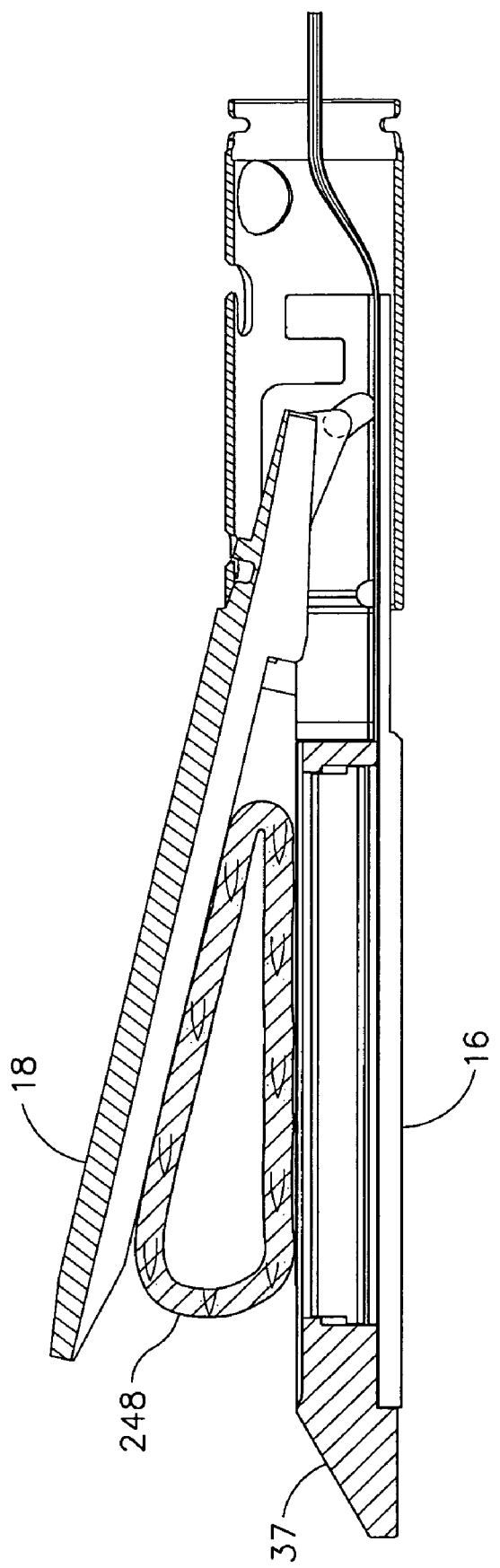
FIG. 20 depicts a side elevation view in centerline section of the surgical stapling and severing instrument of FIG. 1 with the end effector in a partially closed but unclamped position gripping tissue according to various embodiments of the present invention.

In use, the surgical stapling and severing instrument 10 is used as depicted in FIGS. 1, 2, and 20-26. In FIGS. 1-2, the instrument 10 is in its start position, having had an undriven, fully loaded staple cartridge 37 snap-fitted into the distal end of the elongate channel 16. Both triggers 26, 28 are forward and the end effector 12 is open, such as would be typical after inserting the end effector 12 through a trocar or other opening into a body cavity. The instrument 10 is then manipulated by the clinician such that tissue 248 to be stapled and severed is positioned between the staple cartridge 37 and the anvil 18, as depicted in FIG. 20.

Figure 21:
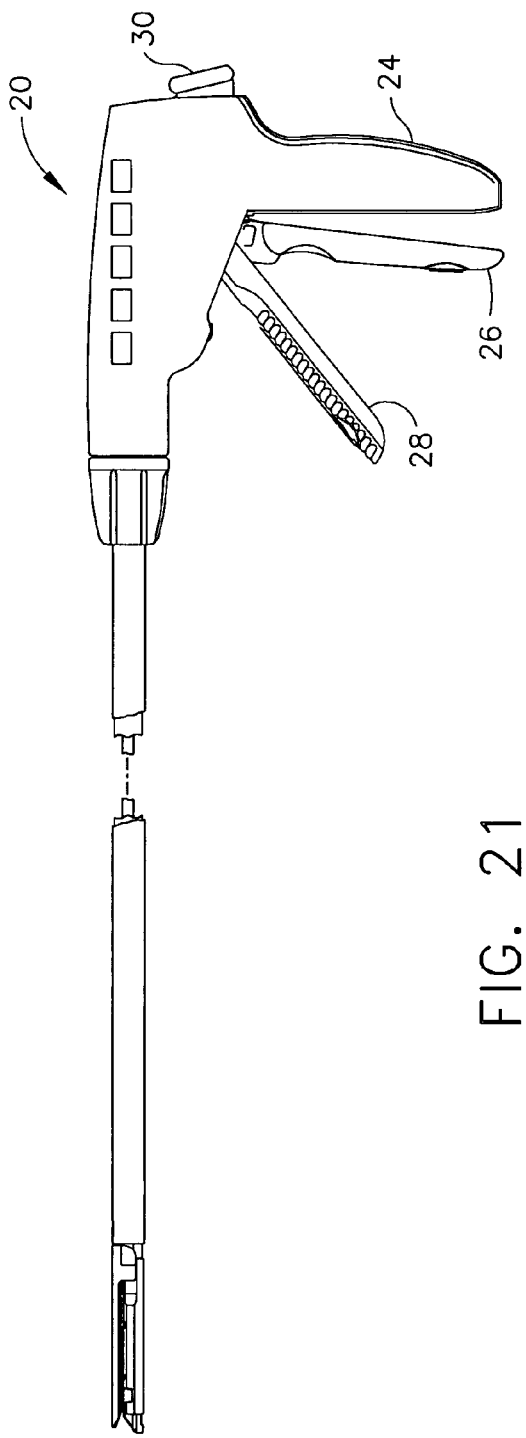
FIG. 21 depicts a partially cut-away side elevational view of the surgical stapling and severing instrument of FIG. 1 in the closed or clamped position according to various embodiments of the present invention.
Figure 22:
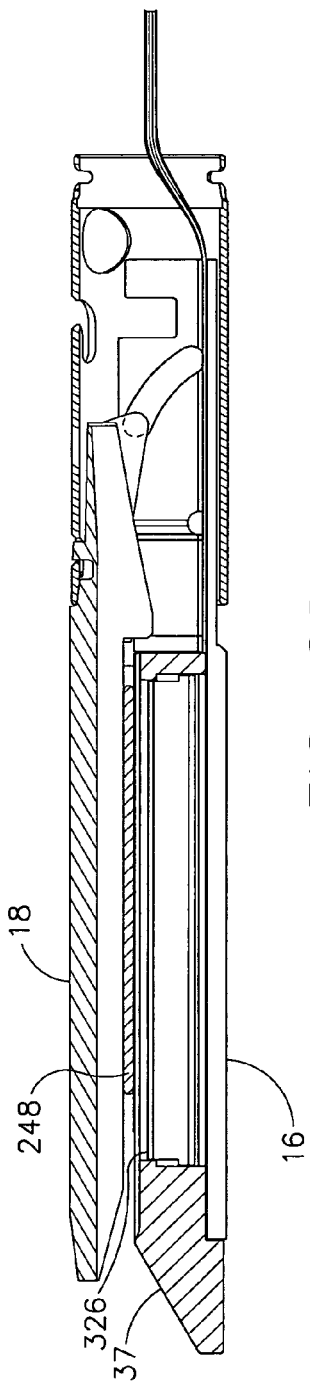
FIG. 22 depicts a side elevation view in centerline section of the distal end of the surgical stapling and severing instrument of FIG. 1 in the closed or clamped position with tissue properly compressed according to various embodiments of the present invention.

With reference to FIGS. 21-22, next, the clinician moves the closure trigger 26 proximally until positioned directly adjacent to the pistol grip 24, locking the handle portion 20 into the closed and clamped position. The retracted cutting edge 326 in the end effector 12 does not impede the selective opening and closing of the end effector 12, but rather resides along the elongate channel 16, positioned in the slot 49 of the staple cartridge 37. In response to the actuation of the closure trigger 26, the anvil 18 may be driven to pivot along anvil pivot 14.

Figure 23:
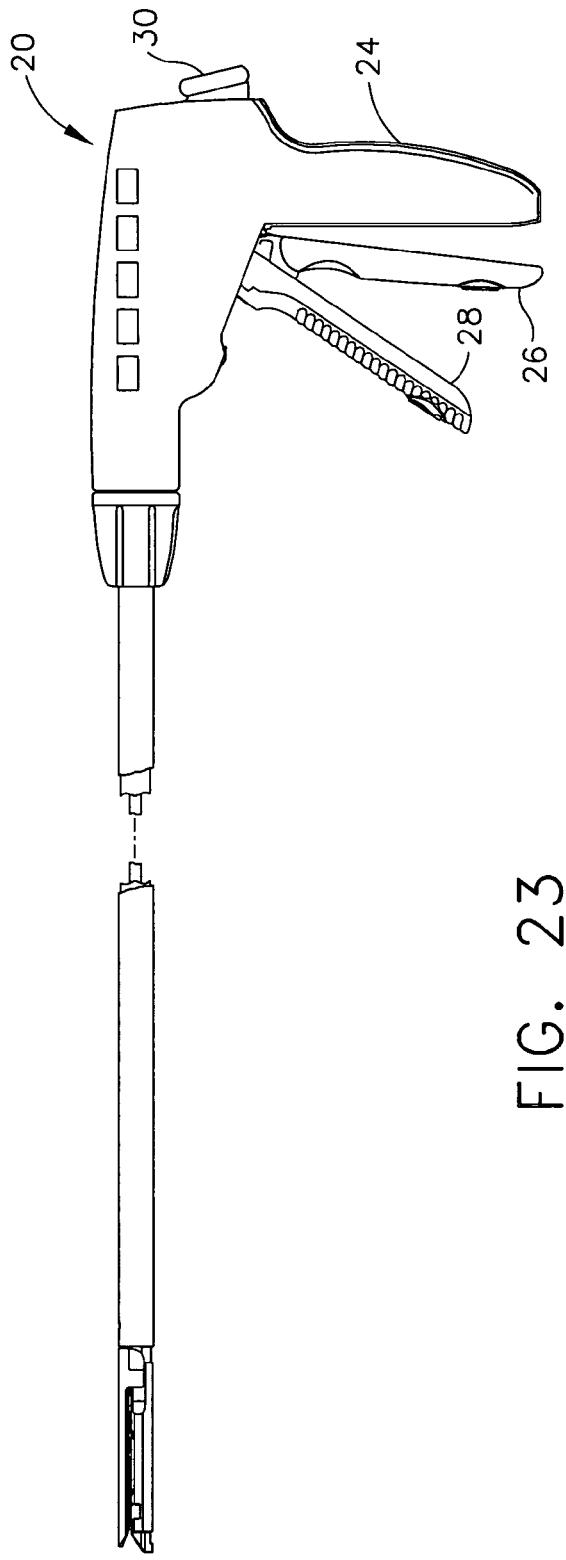
FIG. 23 depicts a partially cut-away side elevation view of the surgical stapling and severing instrument of FIG. 1 in a partially fired position according to various embodiments of the present invention.
Figure 24:
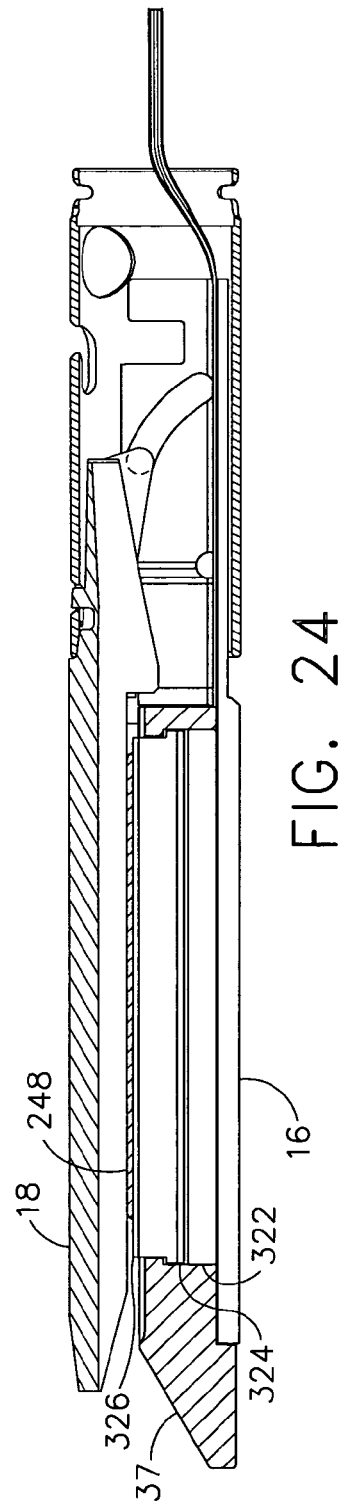
FIG. 24 depicts a side elevation view in centerline section of the distal end of the surgical stapling and severing instrument of FIG. 1 in a partially fired position according to various embodiments of the present invention.

With reference to FIGS. 23-24, after tissue clamping has occurred, the clinician moves the firing trigger 28 proximally causing hydraulic fluid to be pressurized, for example, by hydraulic pump 302. When the instrument is configured to cut, the hydraulic pressure may cause cutting bladder 322 to inflate, forcing cutting bar 324 through slot 49 and into contact with cutting edge 326, which may sever the tissue 248. When the instrument is configured to staple, the hydraulic pressure may cause one or more of the staple bladders 328, 330, 332, 334, 336, 338 (not shown in FIG. 24) to inflate, exerting a vertical force on drivers 220 which in turn drive staples 222. With reference to FIGS. 25-26, the clinician continues moving the firing trigger 28 until brought proximal to the closure trigger 26 and pistol grip 24. Thereby, all of the ends of the staples 222 are bent over as a result of their engagement with the anvil 18. The process is completed by releasing the firing trigger 28 and by then depressing the release button 30 while simultaneously squeezing the closure trigger 26 to open the end effector 12.

While the present invention has been illustrated by description of several embodiments and while the illustrative embodiments have been described in considerable detail, it is not the intention of the applicant to restrict or in any way limit the scope of the appended claims to such detail. Additional advantages and modifications may readily appear to those skilled in the art.

For example, although the embodiments described above have advantages for an endoscopically employed surgical severing and stapling instrument 10, a similar embodiments may be used in other clinical procedures. It is generally accepted that endoscopic procedures are more common than laparoscopic procedures. Accordingly, the present invention has been discussed in terms of endoscopic procedures and apparatus. However, use herein of terms such as "endoscopic", should not be construed to limit the present invention to a surgical instrument for use only in conjunction with an endoscopic tube (i.e., trocar). On the contrary, it is believed that the present invention may find use in any procedure where access is limited to a small incision, including but not limited to laparoscopic procedures, as well as open procedures.

For yet another example, although an illustrative handle portion 20 described herein is operated hydraulically in response to input from a clinician, it is consistent with aspects of the invention for some or all of the functions of a handle portion to be powered by other means (e.g., pneumatic, electromechanical, ultrasonic, mechanical, etc.). Furthermore, controls of each of these functions may be manually presented on a handle portion or be remotely controlled (e.g., wireless remote, automated remote console, etc.).

Any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

We claim:

1. A hydraulically actuated surgical instrument, the instrument comprising:
    a handle portion;
    a shaft having a longitudinal axis, the shaft mechanically coupled to the handle;
    an end effector mechanically coupled to the shaft along the longitudinal axis, the end effector comprising:
        a first jaw member extending from the distal end of the shaft in a direction substantially parallel to the longitudinal axis; and
        a second jaw member pivotable towards the first jaw member;
        wherein the first jaw member comprises:
            a surgical fastener, at least a portion of the surgical fastener translatable along a transverse axis towards the second jaw member, wherein the transverse axis is substantially perpendicular to the longitudinal axis;
            a hydraulic device positioned to be expandable toward the surgical fastener in a direction substantially parallel to the transverse axis to actuate the surgical fastener;
            a surgical cutting edge extending along the longitudinal axis, at least a portion of the surgical cutting edge translatable towards the second jaw member in a direction substantially perpendicular to the longitudinal axis; and
            a second hydraulic device positioned to be expandable toward the surgical cutting edge in a direction substantially perpendicular to the longitudinal axis to actuate the surgical cutting edge.

2. The instrument of claim 1, wherein the hydraulic device is selected from the group consisting of a hydraulic bladder and a hydraulic cylinder.

3. The instrument of claim 1, wherein the shaft is rigid, and wherein the rigid shaft comprises an articulation pivot, whereby the end effector pivots away from the longitudinal axis at the articulation pivot.

4. The instrument of claim 1, wherein the surgical fastener comprises a staple cartridge comprising a staple oriented in a first direction, and wherein the hydraulic device is positioned to be expandable in the first direction toward the staple.

5. The instrument of claim 4, further comprising a staple driver positioned between the hydraulic device and the staple.

6. The instrument of claim 1, further comprising a control circuit connected to cause actuation of the hydraulic device and the second hydraulic device wherein the control circuit is configured to:
    receive an input signal; and
    in response to the input signal, actuate the hydraulic device and, after a predetermined delay, actuate the second hydraulic device.

7. The instrument of claim 1, wherein the first hydraulic device comprises a hydraulic cylinder comprising a piston extendible along the transverse axis.

* * * * *